US011628053B2

(12) United States Patent
Forsell

(10) Patent No.: US 11,628,053 B2
(45) Date of Patent: Apr. 18, 2023

(54) VARIABLE SLING FOR URINARY CONTINENCE

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/123,037

(22) PCT Filed: Oct. 12, 2009

(86) PCT No.: PCT/SE2009/000447
§ 371 (c)(1),
(2), (4) Date: Apr. 7, 2011

(87) PCT Pub. No.: WO2010/042010
PCT Pub. Date: Apr. 15, 2010

(65) Prior Publication Data
US 2011/0201873 A1 Aug. 18, 2011

Related U.S. Application Data

(60) Provisional application No. 61/136,887, filed on Oct. 10, 2008.

(51) Int. Cl.
*A61F 2/00* (2006.01)
(52) U.S. Cl.
CPC .... *A61F 2/0045* (2013.01); *A61F 2250/0001* (2013.01); *A61F 2250/0004* (2013.01)
(58) Field of Classification Search
CPC .... A61F 2/0004; A61F 2/0007; A61F 2/0045; A61F 2/0031; A61F 2/0036; A61F 2/0063; A61F 2250/0001; A61B 2017/00805; A61B 2560/0214; A61B 2560/0219
USPC ................ 600/29–32, 37; 128/885, DIG. 25; 606/151
See application file for complete search history.

(56) References Cited

U.S. PATENT DOCUMENTS

| 6,074,341 A | 6/2000 | Anderson et al. |
| 7,395,822 B1 | 7/2008 | Burton et al. |
| 2002/0028980 A1 | 3/2002 | Thierfelder et al. |
| 2003/0105385 A1* | 6/2003 | Forsell ........................ 600/29 |
| 2005/0004576 A1* | 1/2005 | Benderev ..................... 606/72 |
| 2006/0189888 A1* | 8/2006 | Hassler ............. A61M 39/0208 |
| | | 600/561 |

(Continued)

FOREIGN PATENT DOCUMENTS

| EP | 1 598 030 | 11/2005 |
| WO | 96/01597 A2 | 1/1996 |
| WO | WO 2007/149555 | 12/2007 |

OTHER PUBLICATIONS

International Search Report for PCT/SE2009/000447, dated Jan. 28, 2010.

(Continued)

*Primary Examiner* — Carrie R Dorna

(57) ABSTRACT

An apparatus for treating urinary incontinence in a patient includes at least one adjustable lifting device for supporting a patient's urethra to restore urinary control. The adjustable lifting device can post-operatively and non-invasively adjust the level of lift of a patient's urethra, to thereby affect the patient's incontinence. The adjustable lifting device is placed above the pubis bone of the patient. The device includes first and second fixation devices that are adjustable to thereby adjust the length of a sling that cradles and lift's the patient's urethra. The apparatus could also be used to treat anal incontinence.

22 Claims, 15 Drawing Sheets

(56) References Cited

U.S. PATENT DOCUMENTS

2007/0049790 A1 3/2007 Wagner et al.
2008/0269548 A1 10/2008 Vecchiotti et al.

OTHER PUBLICATIONS

Written Opinion of the International Searching Authority for PCT/SE2009/000447, dated Jan. 28, 2010.

* cited by examiner

VARIABLE SLING FOR URINARY CONTINENCE

This application is the U.S. national phase of International Application No. PCT/SE2009/000447 filed 12 Oct. 2009 which designated the U.S. and claims the benefit of U.S. 61/136,887 filed 10 Oct. 2008, the entire contents of each of which are hereby incorporated by reference.

The present invention relates to urinary incontinence, and more particularly, to a method and apparatus for adjusting the level of lift provided by a thread or sling implanted in a patient to lift the patient's urethra.

BACKGROUND OF THE INVENTION

Urinary incontinence is a condition in which a person is unable to control the flow of urine from his or her bladder. In women, the sphincter muscle is located below the bladder, surrounding the urethra. When the sphincter muscle tightens, it closes the urethra and holds urine in the bladder. When it relaxes, the bladder contracts and the urethra opens, allowing urine to flow from the bladder. To operate properly, the bladder and urethra must be properly supported by the pelvic muscles and tissue. Urinary incontinence usually occurs because a urethra cannot be closed tightly enough to hold urine in the bladder.

There are surgical options for treating urinary incontinence. One operation includes a procedure in which a sling is implanted in a patient to serve as a support for the urethra during increased abdominal pressure. In the sling procedure, the urethra is lifted a specified amount using a fixed thread or band of a set length. The result obtained with this kind of operation can be fairly good, but a more desirable result could be obtained if it were possible to post-operatively and non-invasively adjust the level of lift provided by the urethra sling, to achieve, with minimum side effects, a desired level of continence. There is one product available that can be used to post-operatively adjust the level that a urethra is lifted. However, this product can only be adjusted invasively, and thus, it has never been very successful because of the high risk of infection associated with opening the skin over an implant. If such an infection occurs, it can be very difficult to treat without taking out the implant. Thus, it would be desirable to provide a sling device that can be used to post-operatively and non-invasively adjust the level of lift of a urethra.

SUMMARY OF THE INVENTION

The present invention is directed to an apparatus for treating urinary incontinence in a patient that includes at least one adjustable lifting device for supporting a patient's urethra or neck of the urine bladder to restore urinary control. The adjustable lifting device is adapted to post-operatively and non-invasively adjust the level of lift of a patient's urethra, to thereby affect the patient's incontinence. The adjustable lifting device is adapted to be placed, at least partially, in a female or male patient in one of several locations, i.e., below the pubis bone, so as to lift the urethra from a point below the pubis bone when the patient is standing, into the pubis bone, so as to lift the urethra from a point attached to the pubis bone of the patient, or above the pubis bone of the patient, so as to lift the urethra from a point above the pubis bone when the patient is standing.

The apparatus may further include a first fixation device, wherein the lifting device adjusts the distance between a first fixation position of the device and the urethra, and wherein the first fixation device is preferably attached to the pubis bone of the patient.

The apparatus may also include a second fixation device, wherein the lifting device adjusts the distance between a second fixation position of the device and the urethra, and wherein the second fixation device is preferably attached to the pubis bone of the patient.

The first fixation or second fixation are preferably adjustable, however, the first fixation and/or second fixation device can keep the device in place by sutures or staples between the device and human tissue or bone.

Alternatively, the first fixation and/or second fixation devices are connected in a loop and keep the device in place by the loop, which can include human tissue. In this embodiment, the lifting device is adjusted by changing the size of the loop so that the loop adjustment adjusts the lift of the urethra.

The device may also be kept in place by invagination of human tissue by tissue-to-tissue sutures or staples.

The lifting device also includes an interconnecting part that connects the first and second fixation devices to each other. The lifting device lifts the urethra or neck of the urine bladder by changing the length of the interconnecting part, when implanted. The interconnecting part preferably has a u-shaped form that cradles the urethra when implanted in a patient. The urethra is lifted by reducing the length of the u-shaped interconnecting part. Normally the device forms a loop and the adjustment changes the length of the loop to lift the urethra. The loop can have any shape or form that can be used to lift the urethra when placed inside the loop, when implanted. The device forms a loop that is placed around stable tissue. The loop holds up the urethra, when placed inside the loop, when implanted. Preferably, the interconnecting part is a band or a thread, or a plurality of bands or threads connected to each other to lift the urethra.

The interconnecting part may include an adjustable part, adapted to make contact with the urethra or neck of the urine bladder or surrounded associated tissue to the urethra or bladder neck and adapted to change at least one of the length and diameter of the adjustable part.

The adjustable part may be adapted to change the length of the adjustable part.

The adjustable part may also be adapted to change the width of the adjustable part.

The interconnecting part may include an adjustable part, comprising a hydraulic adjustment, wherein the adjustable part comprise a fillable reservoir adapted to be filled with a fluid from a second reservoir so as to adjust at least one of the length and diameter of the adjustable part.

Another treatment area include an apparatus to treat anal incontinence in a patient, comprising at least one adjustable lifting device adapted to lift the rectum or anal channel, thereby affecting the patient's incontinence, the at least one adjustable lifting device comprising first and second fixation devices and an interconnecting part extending uninterruptedly between the first and second fixation devices, wherein the at least one lifting device is adapted to post-operatively and non-invasively adjust the level of lift of the rectum or anal channel by changing at least one of the length and width of the interconnecting part.

Please note that any embodiment part of embodiment or feature or method or step of method that is applicable or not contradictive and described for urinary incontinence could also be used for anal incontinence, both regarding description, claims and detailed description.

Alternatively, the first fixation and/or second fixation devices include a structure adapted to be in contact with human tissue to promote growth of human tissue in the structure, to thereby secure the long term placement of the lifting device in a patient. Preferably, the structure is a net-like structure.

Normally, the device is non-circumferential, and is adapted to be non-invasively adjustable, post-operatively by the patient.

Preferably, the first and second fixation devices have a screw member to hold the devices in place with a screw inserted into the pubis bone.

The apparatus may further comprise a subcutaneous switch, that can be manually and non-invasively operated by manually pressing the switch to regulate the lifting device. The lifting device may also be a hydraulically or pneumatically regulated device that includes at least one chamber and a hydraulic or pneumatic reservoir. The device can be non-invasively regulated by moving liquid or air from the reservoir to the chamber. The reservoir is regulated by manually pressing the reservoir.

The apparatus may also comprise a reversible servo, in which a small volume in the reservoir is compressed using a high force and the chamber creates a movement of a larger total area with less force per area unit.

Preferably, the reservoir is placed subcutaneously or in the abdomen of a patient.

The reservoir may be regulated by moving a wall of the reservoir and may comprise a motor that moves the wall of the reservoir. Alternatively, the reservoir is regulated by a pump pumping fluid or air from the reservoir to the chamber. The hydraulically or pneumatically regulated lifting device may also comprise a mechanical device that is regulated by the hydraulic or pneumatic movement of fluid or air or a mechanically regulated lifting device or a motor for mechanically regulating the lifting device.

The apparatus may also include a mechanical device that regulates the distance between the first and second fixation devices attached to the stomach wall. In one alternative, the mechanical device connects the first and second fixation devices onto the pubis bone. Alternatively, a mechanical device connects the first and second fixation devices by the interconnecting part.

The apparatus may comprise an operation device for operating the lifting device, wherein the operation device comprises at least one motor or pump.

The apparatus may comprise a wireless energy transmitter for transmitting wireless energy for use by any energy consuming part of the device, directly or indirectly. The energy-transmission device transmits energy by at least one wireless energy signal. The apparatus preferably comprises an operation device to adjust the device, wherein the transmitted energy, which is a first form energy in its wireless form, directly affects the operation device to create kinetic energy to adjust the lifting device during energy transfer. Preferably, a motor creates the kinetic energy, directly, using the wireless energy in its first form.

The present invention is also directed to methods for treating urinary incontinence using an adjustable lifting device for adjusting a urethra post-operatively and non-invasively.

A surgical method for treating a urinary incontinent patient using the apparatus described above includes the steps of (a) cutting an opening in the skin of the patient; (b) dissecting the area around the urethra or the urine bladder and the area to place the fixation members onto the pubis bone or softer tissue, (c) implanting at least one non-invasively adjustable lifting device for lifting the urethra neck of the urine bladder or the urine bladder, (d) attaching the fixation members, and (e) closing, if necessary, the wounds caused by the cutting and/or dissecting.

Alternatively, a vaginal surgical method for treating a urinary incontinent patient using the apparatus described above includes the steps of (a) cutting an opening in the vaginal wall, (b) dissecting the area around the urethra or the urine bladder and the area to place the fixation members onto the pubis bone or softer tissue, (c) implanting at least one non-invasively adjustable lifting device for lifting the urethra, neck of the urine bladder or urine bladder, (d) attaching the fixation members, and (e) closing, if necessary, the wounds caused by the cutting and/or dissecting.

The methods described above further include the steps of post-operatively and non-invasively regulating the lifting device to (a) adjust the length of a lifting sling part of the lifting device to adjust the lift of the urethra or the urine bladder, and (b) regulate the device non-invasively from outside the patients body to control the urinary incontinence of the patient.

The methods described above further include the steps of attaching the fixation members and dissecting subcutaneously or in a muscle or further inside the body in relation to the muscle to implant an operation device for adjusting the lifting device. The step of implanting the fixation members comprises the steps of (i) implanting the operation device in the dissected area, and (ii) operating the operation device non-invasively and post-operatively.

A laparoscopic surgical method for treating a urinary incontinent patient using the apparatus described above comprises the steps of (a) inserting a needle-like tube into the patient's body, (b) using the needle-like tube to fill a cavity within the patient's body with gas, to thereby expand the cavity, (c) placing at least two laparoscopic trocars in the patient's body in the cavity, (d) inserting a camera through one of the trocars into the cavity, (e) inserting at least one dissecting tool through a trocar and dissecting an area of at least one portion of the region of the urethra or urine bladder of the patient, (f) placing at least one lifting device on the urethra or neck of the urine bladder, (g) adjusting the device post operatively and non-invasively, and (h) controlling the adjustment from outside the patients body to control the urinary incontinence of the patient.

The adjusting device may be regulated non-invasively by, for example, (a) manually pressing a switch, (b) using a hydraulic or pneumatic regulated lifting device comprising a hydraulic or pneumatic reservoir connected to the lifting device, the non-invasively regulation being performed by manually pressing the reservoir, (c) using a wireless remote control, the non-invasively adjustment being performed by the remote control, or (d) using a wireless energy transmitter, the non-invasively adjustment being performed by the energy transmitter.

The method preferably includes an energy source for powering the adjustable lifting device. The energy source may comprise an internal energy source or an external energy source transmitting wireless energy, wherein the external energy source may in some embodiments charge an internal energy source that is rechargeable.

The method may alternatively include a lifting device that is comprised of a mechanical device or hydraulic device. The lifting device will be powered by an energy source, the power being controlled from outside the patient's body.

The wireless transfer of energy preferably powers the lifting device directly during energy transfer so as to cause the device to adjust the lift of the urethra or urine bladder or the neck of the urine bladder.

Another aspect of the method comprises feedback information being sent from inside the body to the outside thereof to give feed back related to the functional parameters of the lifting device or physical parameters of the patient. Preferably, the functional parameters of the lifting device are correlated to a transfer of energy for charging an internal energy source.

Preferably, the method includes programming the lifting device, which is programmable from outside of the patient's body.

The method may further comprise the steps of (a) sensing a physical parameter of the patient or a functional parameter of the adjustment device, and (b) sending sensing information to a control unit adapted for controlling the adjustment device. The sensing information may be used for regulating the charging of the internal energy source.

The method of regulation preferably includes an operation device for controlling the adjustable lifting device, which preferably comprises a motor. The method may include directly operating the motor with a wireless energy field to directly change wireless energy into kinetic energy for control of the adjustable lifting device.

BRIEF DESCRIPTION OF THE DRAWINGS

The present invention will now be described in more detail by way of non-limiting examples and with reference to the accompanying drawings, in which:

FIG. 4A is an alternative cross sectional view of the apparatus of FIG. 1 for treating urinary incontinence in a patient that includes an adjustable lifting device, but attached to the patient's muscle for supporting the patient's urethra.

DETAILED DESCRIPTION OF PREFERRED EMBODIMENTS

Figure 1:
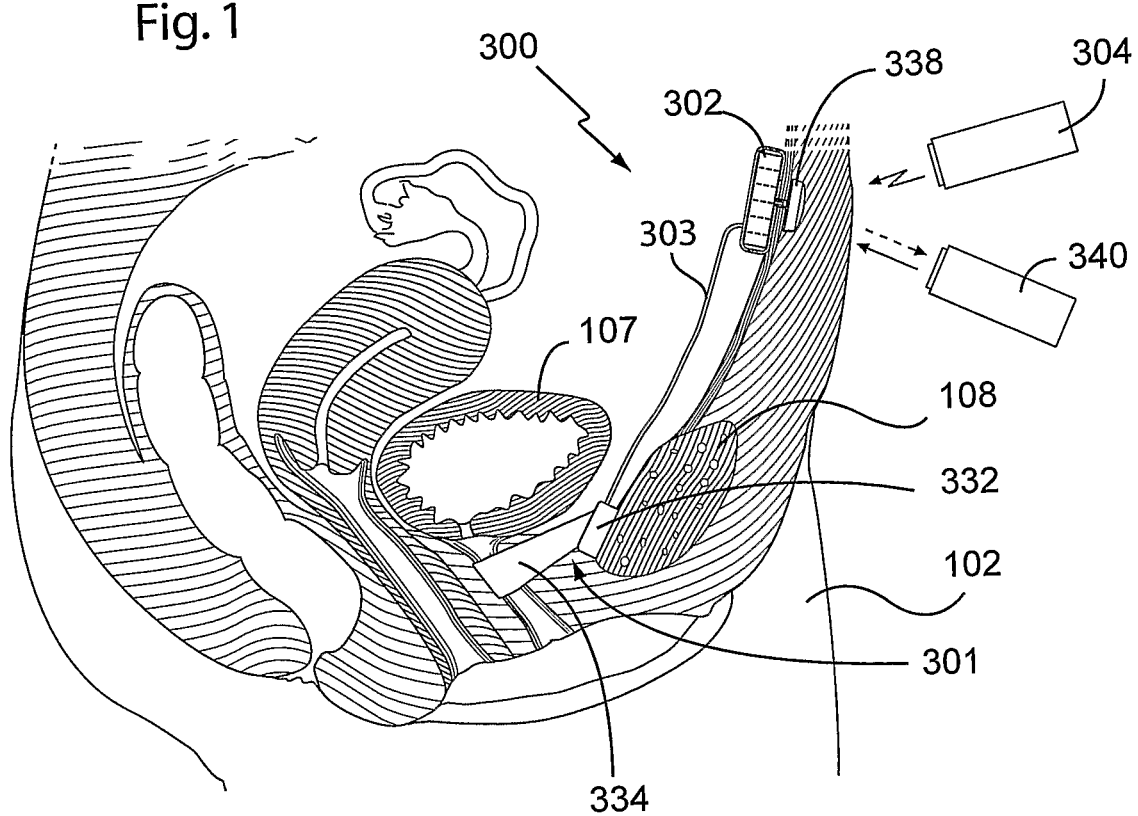
FIG. 1 is a cross sectional view of an apparatus for treating urinary incontinence in a patient that includes an adjustable lifting device attached to the patient's pubis bone for supporting the patient's urethra.
Figure 2:
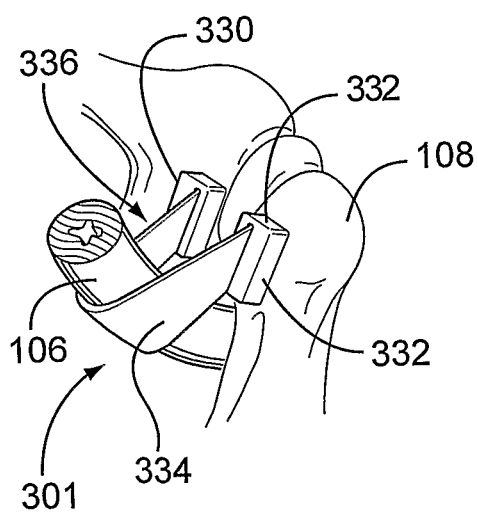
FIG. 2 is a perspective view of the adjustable lifting device shown in FIG. 1 attached to the patient's pubis bone for supporting the patient's urethra.

FIG. 1 is a cross sectional view showing a apparatus 300 for treating urinary incontinence that is implanted in a patient 102. The apparatus 300 includes at least one adjustable lifting device 301 attached to the patient's pubis bone 108 for supporting the patient's urethra 106 to restore urinary control of the patient's bladder 107. FIG. 2 is a perspective view showing the adjustable lifting device 301 of FIG. 1 attached to the patient's pubis bone 108 for supporting the patient's urethra 106. The adjustable lifting device 301 can be post-operatively and non-invasively controlled to adjust the level of lift of the patient's urethra 106 to thereby affect the patient's incontinence. The adjustable lifting device 301 can be placed, at least partially, in a female or male patient in one of several locations, i.e., below the patient's pubis bone 108, so as to lift the urethra from a point below the pubis bone when the patient 102 is standing, into the pubis bone 108, as shown in FIGS. 1 and 2, so as to lift the urethra 106 from a point attached to the pubis bone 108 of the patient 102, and above the pubis bone 108, so as to lift the urethra 106 from a point above the pubis bone 108 when the patient 102 is standing.

Figure 3:
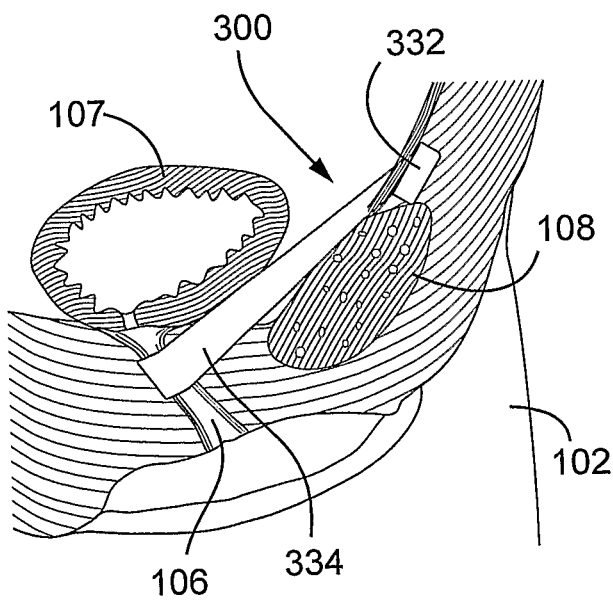
FIG. 3 is a cross sectional view of an apparatus for treating urinary incontinence in a patient that includes an adjustable lifting device attached above the patient's pubis bone for supporting the patient's urethra.

FIG. 3 is a cross sectional view showing the apparatus 300 for treating urinary incontinence implanted in a patient in which the adjustable lifting device 301 is attached above the patient's pubis bone 108 for supporting the patient's urethra 106.

The apparatus 300 may comprise a subcutaneous switch 338 that can be manually and non-invasively operated by manually pressing the switch 338 to regulate the lifting device 301. The subcutaneous switch 338 can be mounted on an implanted device 302 located behind a patient's abdomen. The lifting device 301 may also be a hydraulically or pneumatically regulated device that includes at least one chamber and a hydraulic or pneumatic reservoir. The lifting device 301 can be non-invasively regulated by moving liquid or air from the reservoir to the chamber. The reservoir can be regulated by manually pressing the reservoir using a button attached to the implanted device 302, like the switch 338 shown in FIG. 1.

The adjustable lifting device 301 may further comprise a first fixation device 330, so that the lifting device 301 is adapted to adjust the distance between a first fixation position of the first fixation device 330 and the urethra 106, wherein the first fixation device 330 is preferably attached to the pubis bone 108 of the patient 102.

The apparatus may also comprise a second fixation device 332, so that the lifting device 301 is adapted to adjust the distance between the second fixation position of the second fixation device 332 and the urethra 106, wherein the second fixation device 332 is preferably attached to the pubis bone 108 of the patient 102.

Preferably, the first and second fixation devices 330 and 332 each have a screw member (not shown) to hold the lifting device 301 in place with a screw (not shown) into the pubis bone 108.

The first fixation and second fixation devices 330 and 332 are adjustable, and in one embodiment, the first fixation and/or second fixation devices are adapted to keep the adjustment device 301 in place by sutures or staples between the devices and the human tissue or bone, as shown in FIG. 3.

Alternatively the first fixation and/or second fixation devices are connected in a loop and adapted to keep the adjustable lifting device 301 in place by the loop including human tissue. The lifting device 301 is adjusted by changing the size of the loop so that the loop adjustment adjusts the lift of the urethra 106. The adjustable lifting device 301 may be adapted to be kept in place by invagination of human tissue by tissue-to-tissue sutures or staples.

The apparatus 300 also comprises an interconnecting part 334 that connects the first and second fixation devices 330 and 332 to each other. The interconnecting part 334 can be a thread or a sling or a plurality of threads or slings that is/are made from a synthetic and/or biological material. The adjustment device 301 lifts the urethra 106 by changing the length of the interconnecting part 334, when implanted. Typically, the interconnecting part 334 has a u-shaped form, as best seen in FIG. 2, that cradles the urethra 106 when the lifting device 301 is implanted in a patient 102. The adjustable lifting device 301 lifts the urethra 106 by reducing the length of the u-shaped interconnecting part 334. Normally, the interconnecting part 334 forms a loop 336, and the adjustable lifting device 301 changes the length of the loop 336, to thereby change the lift of the urethra 106. The loop 336 of the interconnecting part 334 can have any shape or form that can be used to lift the urethra 106, when the urethra 106 is placed inside the implanted loop 336. The device 301 can form the loop 336 around stable tissue of the patient 102 so that the loop 336 holds up the urethra 106, when it is placed inside the implanted loop 336.

Alternatively the first fixation and/or second fixation devices 330 and 332 comprise a structure adapted to be in contact with human tissue to promote growth of human tissue in the structure of devices 330 and 332 to secure the long term placement of the devices 330 and 332 in a patient 102. Preferably, this structure is a net-like structure.

Normally, the device 301 is non-circumferential. The device 301 is non-invasively adjustable post-operatively by the patient using an implanted device 302 shown in FIGS. 1 and 4a.

Figure 4A:
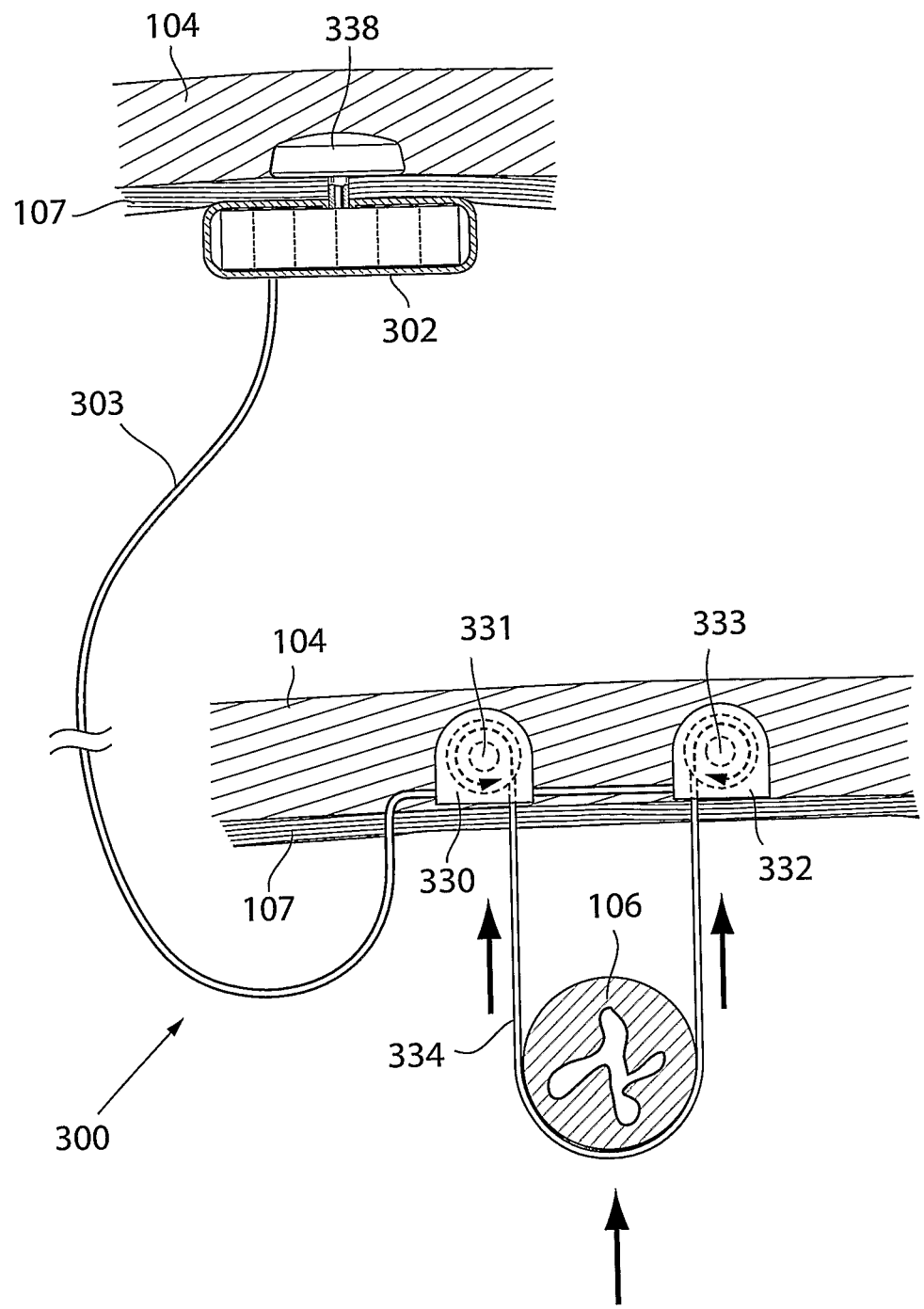
FIGS. 4A and 4B are a simplified illustration of the apparatus for controlling and powering the adjustable lifting device shown in FIGS. 1 to 3 that is implanted in a patient.

FIG. 4A is an alternative cross-sectional view showing apparatus 300 for supporting the urethra 106 of a patient 102 to restore urinary control of the patient's bladder. In the arrangement shown in FIG. 1A, the first and second fixation devices 330 and 332 are shown as being connected to a muscle 107 and as including electromechanical devices 331 and 333, respectively, that are used to shorten the length of interconnecting part 334 so as to change the amount of lift or urethra 106 provided by lifting device 301. As depicted in FIG. 1A, electromechanical devices 331 and 332 are caused by implanted control switch 302 to rotate counter-clockwise and clockwise, respectively, to "wind up" interconnecting part 334, to thereby shorten the length of interconnecting part 334 and increase the lift provided for urethra 106. To perform the winding function, electromechanical devices 331 and 332 can each include an electrical motor attached to a pulley around which the interconnecting part 334 is wound. The motors included in electromechanical devices 331 and 332 are attached to control switch 302 through wire 303.

Figure 31:
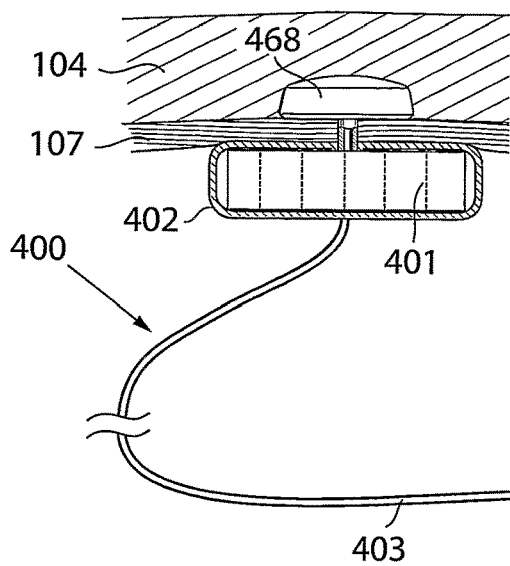
FIG. 31 shows an alternative embodiment for controlling the length of an interconnecting part.
Figure 31:
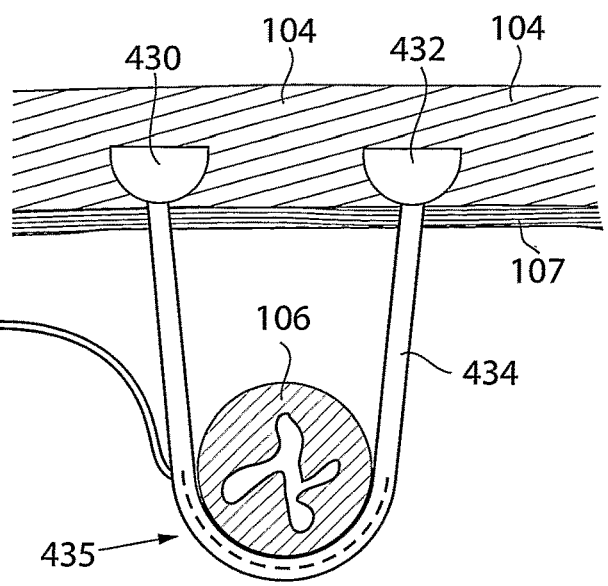
Figure 32B:
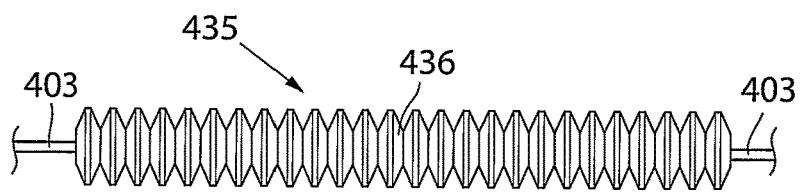
FIGS. 32A and 32B show an interconnecting part in the form of a bellow.
Figure 32A:
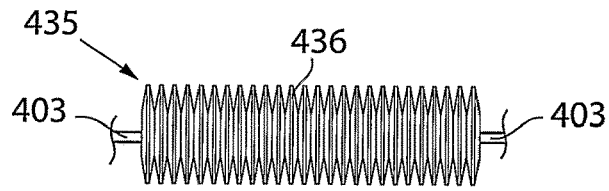
Figure 33B:
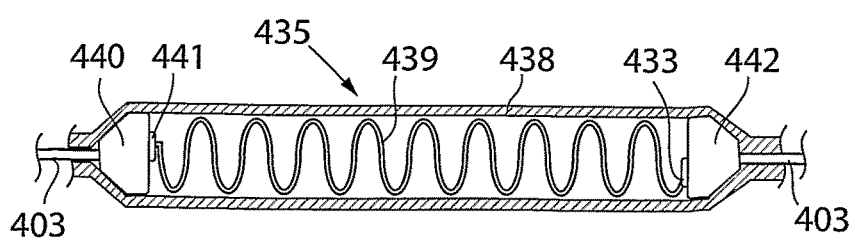
FIGS. 33A and 33B show an interconnecting part comprising a spring.
Figure 33A:
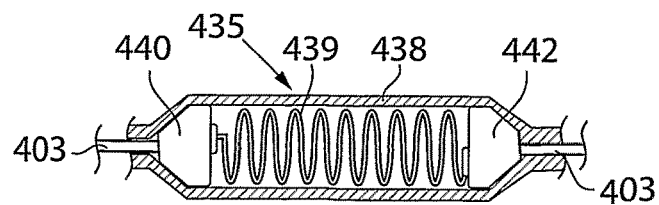

FIG. 31 shows an alternative embodiment for controlling the length of the interconnecting part 334 shown in FIGS. 1-3. In this embodiment, the length of interconnecting part 434 is not changed by winding it around a pulley located within first and second fixation devices, like fixation devices 330 and 332. Rather, interconnecting part 434 includes an adjustable part 435 constructed from either a bellows 436, as shown in FIGS. 32A and 32B, or a spring 439 encased in a tube 438 formed from an elastic material, as shown in FIGS. 33A and 33B. Preferably, the adjustable part 435 of interconnecting part 434 is located in the center of interconnecting part 434, although it should be noted that adjustable part 435 can be skewed to one side or the other of the center of interconnecting part 434. In the embodiment shown in FIG. 31, the interconnecting part 434 is connected between first and second fixation devices 430 and 432 that serve to anchor the ends of interconnecting part 334 to muscle 107 of patient 104.

For the bellows 436 shown in FIGS. 32A and 32B, the apparatus 400 for treating urinary incontinence includes a subcutaneous control 402 containing a reservoir of fluid 401 and a button 403 for changing the level of fluid in reservoir 401. Connected between the reservoir 401 and the bellows 436 is a line 403 for transferring the fluid from the reservoir 401 to the bellows 436. In its deactivated state, as shown in FIG. 32A, the bellows 436 is contracted and has a maximum diameter and a minimum length by reason of the bellows not being filled with fluid from reservoir 401. In its activated state, as shown in FIG. 32B, the bellows 436 is filled with fluid from reservoir 401 so that the bellows 436 is expanded and has a minimum diameter and a maximum length by reason of the bellows being filled with fluid from reservoir 401. The filling of bellows 436 with fluid from reservoir 401 is accomplished by the patient 104 depressing the button 403 of control 402 to force the fluid from reservoir 401 through the line 403 to the bellows 436.

For the spring 439 shown in FIGS. 33A and 33B, the apparatus 400 again includes subcutaneous control 402. But in this instance, control 402 is an electric switch which is connected by line 403, which can be a pair of wires, to at least one motor 440 that is encased in tube 438 and suitably connected to one end 441 of spring 439, also encased in tube 438. The other end 433 of spring 439 is connected to a device 442 which can be either a fixture for holding the end 433 of spring 439 in place or a motor. In its deactivated state, as shown in FIG. 33A, the spring 439 is contracted and has a maximum diameter and a minimum length by reason of the spring 439 not being under any kind of tension. In its activated state, as shown in FIG. 32B, the spring 439 is rotated either by motor 440 alone (where device 442 is a fixture), under the control of subcutaneous switch 402 so as to cause the coils of spring 439 to be compressed so that spring 439 is expanded and has a minimum diameter and a maximum length by reason of its compression due to the rotation by motor 440. Alternatively, spring 439 can be rotated by motor 440 rotating in a first direction, e.g., clockwise, and device/motor 442 rotating in an opposite direction, e.g., counterclockwise, so as to cause the coils of spring 439 to again be compressed so that spring 439 is expanded and again has a minimum diameter and a maximum length by reason of its compression.

By changing the length and diameter of either bellows 436 or spring 439, the overall length of interconnecting part 434 is caused to be changed, as well, thereby changing the lift provided to urethra 106 by apparatus 400. Thus, in the deactivated states of bellows 436 or spring 439, the overall length of interconnecting part 434 is shorter than the length of interconnecting part 434 where the bellows 436 or spring 439 are activated so as to have a maximum length and a minimum diameter. Of course, it should be noted that the length and diameter of bellows 436 and spring 439 can be such that it is somewhere in between the minimums and maximums of the length and diameter of the bellows 436 and spring 439 so as to control the amount of lift provided to urethra 106 by apparatus 400.

Figure 34:
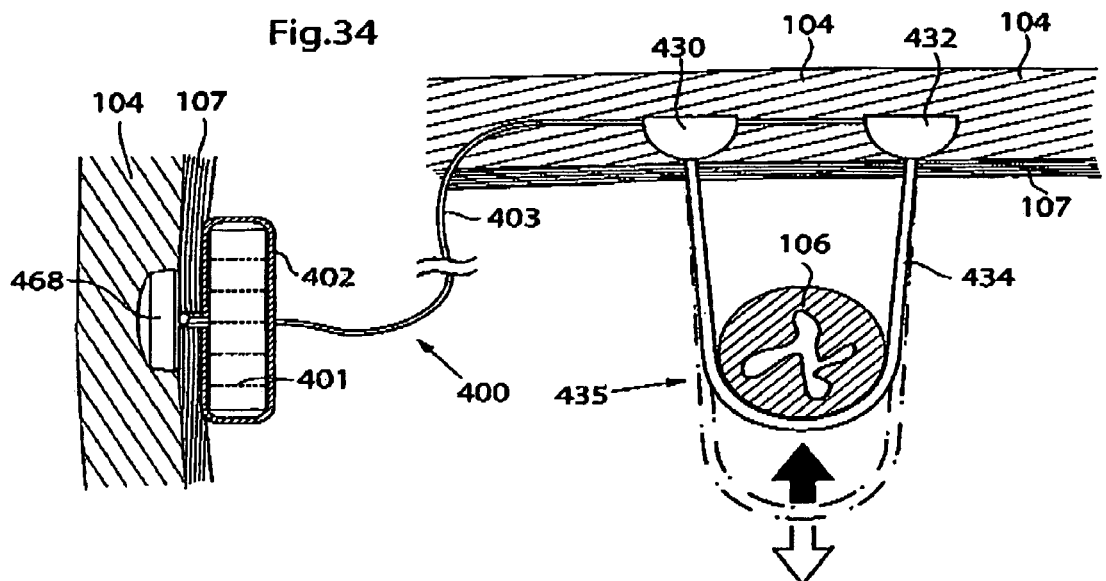
FIG. 34 shows yet an alternative embodiment of a sling wherein essentially the entire sling has an adjustable length.
Figure 35A:
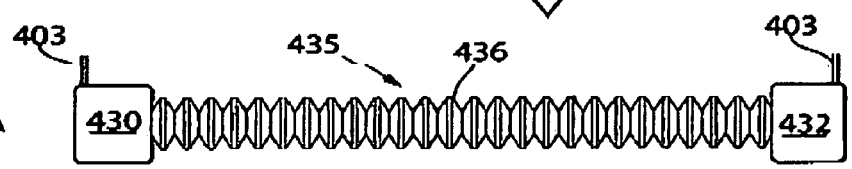
FIGS. 35A and 35B show the sling of 34 in the form of a bellow.
Figure 35B:
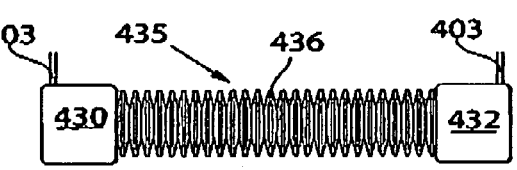
Figure 36A:
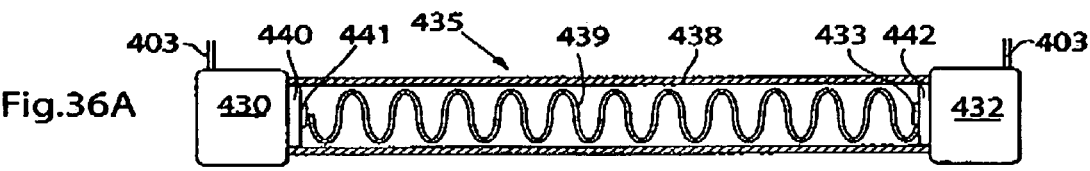
FIGS. 36A and 36B show the sling of 34 comprising a spring.
Figure 36B:
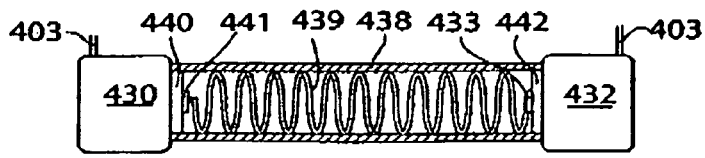

FIG. 34 is similar to FIG. 31. However, the adjustment of the sling now takes place at the fixation devices 430 and 432. FIG. 34 shows an alternative embodiment for controlling the length of the interconnecting, part 334 shown in FIGS. 1-3. In this embodiment, the length of the interconnecting part 434 is changed at the fixation devices, similar to fixation devices 330 and 332 in FIG. 4A. Rather, interconnecting part 434 includes an adjustable part 435 including the adjustable sling constructed from either a bellows 436, as shown in FIGS. 35A and 35B, or a spring 439 encased in a tube 438 formed from an elastic material, as shown in FIGS. 36A and 36B. Preferably, the adjustable part 435 of interconnecting part 434 is located in the whole length of interconnecting part 434. In the embodiment shown in FIG. 34, the interconnecting part 434 is connected between first and second fixation devices 430 and 432 that serve to anchor the ends of interconnecting part 334 to muscle 107 of patient 104.

For the bellows 436 shown in FIGS. 35A and 35B, the apparatus 400 for treating urinary incontinence includes a subcutaneous control 402 containing a reservoir of fluid 401 and a button 468 for changing the level of fluid in reservoir 401. Connected between the reservoir 401 and the bellows 436 is a line 403 for transferring the fluid from the reservoir 401 to the bellows 436. In its deactivated state, as shown in FIG. 35A, the bellows 436 is contracted and has a maximum diameter and a minimum length by reason of the bellows not being filled with fluid from reservoir 401. In its activated state, as shown in FIG. 35B, the bellows 436 is filled with fluid from reservoir 401 so that the bellows 436 is expanded and has a minimum diameter and a maximum length by reason of the bellows being filled with fluid from reservoir 401. The filling of bellows 436 with fluid from reservoir 401 is accomplished by the patient 104 depressing the button 403 of control 402 to force the fluid from reservoir 401 through the line 403 to the bellows 436.

For the spring 439 shown in FIGS. 36A and 36B, the apparatus 400 again includes subcutaneous control 402. But in this instance, the control 402 is an electric switch which is connected by line 403, which can be a pair of wires, to at least one motor 440 that is encased in tube 438 and suitably connected to one end 441 of spring 439, also encased in tube 438. The other end 433 of spring 439 is connected to a device 442 which can be either a fixture for holding the end 433 of spring 439 in place or a motor. In its deactivated state, as shown in FIG. 33A, the spring 439 is contracted and has a maximum diameter and a minimum length by reason of the spring 439 not being under any kind of tension. In its activated state, as shown in FIG. 35B, the spring 439 is rotated either by motor 440 alone (where device 442 is a fixture), under the control of subcutaneous switch 402 so as to cause the coils of spring 439 to be compressed so that spring 439 is expanded and has a minimum diameter and a maximum length by reason of its compression due to the rotation by motor 440. Alternatively, spring 439 can be rotated by motor 440 rotating in a first direction, e.g., clockwise, and device/motor 442 rotating in an opposite direction, e.g., counterclockwise, so as to cause the coils of spring 439 to again be compressed so that spring 439 is expanded and again has a minimum diameter and a maximum length by reason of its compression.

By changing either the length or diameter of either bellows 436 or spring 439, the overall length or diameter of interconnecting part 434 is caused to be changed, as well, thereby changing the lift provided to urethra 106 by apparatus 400. Thus, in the deactivated states of bellows 436 or spring 439, the overall length of interconnecting part 434 is shorter than the length of interconnecting part 434 where the bellows 436 or spring 439 are activated so as to have a maximum length and a minimum diameter. Of course, it should be noted that the length and diameter of bellows 436 and spring 439 can be such that it is somewhere in between the minimums and maximums of the length and diameter of the bellows 436 and spring 439 so as to control the amount of lift provided to urethra 106 by apparatus 400.

Figure 4B:
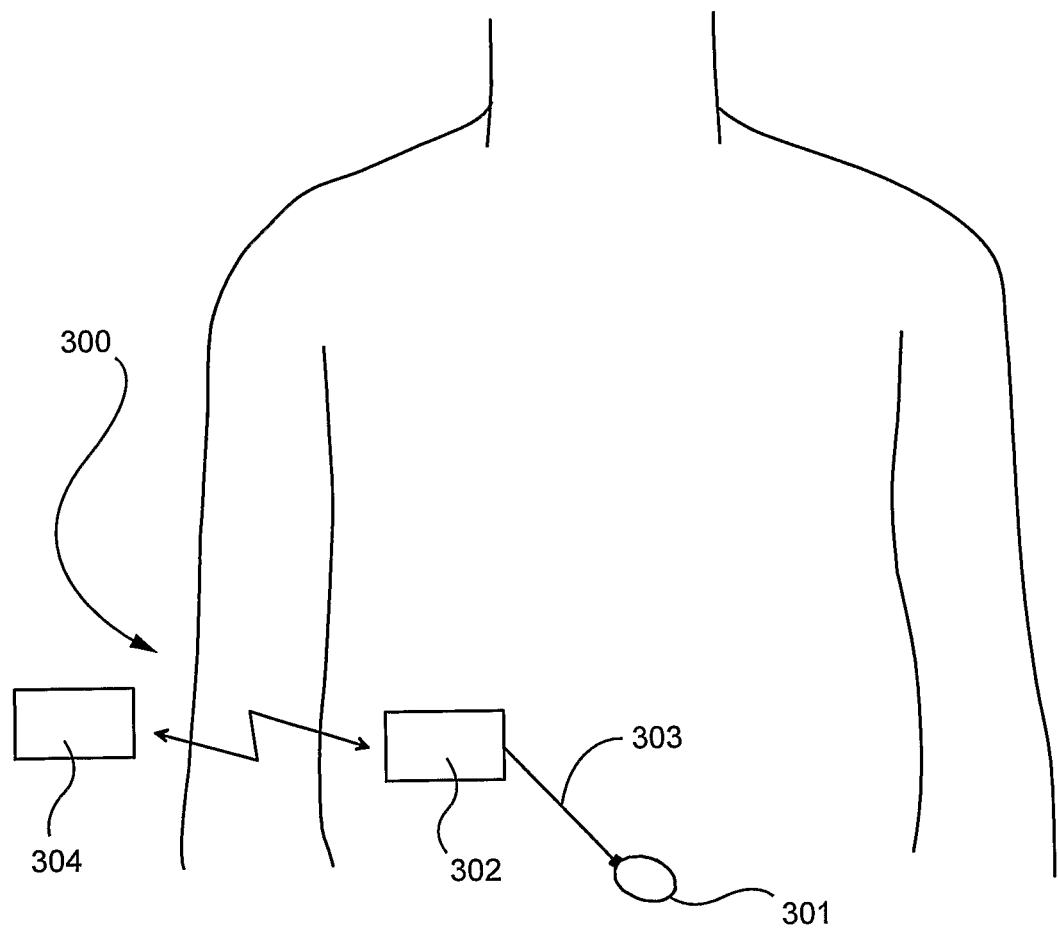

FIGS. 4A and 4B is a simplified illustration of the apparatus 300 for controlling the adjustable lifting device 301. The implanted device 302 used in the apparatus 300 shown in FIG. 4B is an energy-transforming device, which supplies energy consuming components of the lifting device 301 with energy via a power supply line 303. An external energy-transmission device 304 for non-invasively energizing the device 301 transmits energy by at least one wireless energy signal. The implanted energy-transforming device 302 transforms energy from a wireless energy signal into electric energy, which is supplied via the power supply line 303 to the lifting device 301.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted device 301 is operable in response to the energy of the second form. The energy-transforming device 302 may directly power the device 301 with the second form energy, as the energy-transforming device 302 transforms the first form energy transmitted by the energy-transmission device 304 into the second form energy. The lifting device 301 may further include an implantable accumulator, wherein the second form energy is used at least partly to charge the accumulator.

Alternatively, the wireless energy transmitted by the energy-transmission device 304 may be used to directly power the device 301, as the wireless energy is being transmitted by the energy-transmission device 304. Where the adjustable lifting device 301 comprises an operation device for operating the lifting device 301, as will be described below, the wireless energy transmitted by the energy-transmission device 304 may be used to directly power the lifting device 301 to create kinetic energy for the operation of the device 301.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the adjustable lifting device 301 comprises electric components that are energized with electrical energy. Other implantable electric components of the lifting device 301 may include at least one voltage level guard or at least one constant current guard connected with the electric components of the lifting device 301.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device 304 may be controlled from outside the patient's body to release electromagnetic wireless energy, and the released electromagnetic wireless energy is used for operating the lifting device 301. Alternatively, the energy-transmission device 304 is controlled from outside the patient's body to release non-magnetic wireless energy, and the released non-magnetic wireless energy is used for operating the lifting device 301.

The external energy-transmission device 304 also includes a wireless remote control having an external signal transmitter for transmitting a wireless control signal for non-invasively controlling the lifting device 301. The control signal is received by an implanted signal receiver which may be incorporated in the implanted energy-transforming device 302, or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control 304 may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control 304 preferably transmits an electromagnetic carrier wave signal for carrying the digital or analogue control signals.

Figure 5:
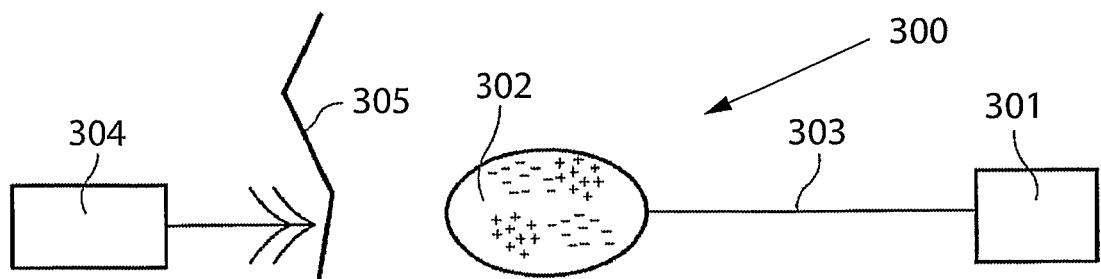
FIGS. 5-19 schematically show various embodiments of the apparatus for wirelessly powering the lifting device shown in FIGS. 1-3.

FIG. 5 illustrates the apparatus of FIG. 4 in the form of a more generalized block diagram showing the adjustable lifting device 301, the energy-transforming device 302 powering the lifting device 301 via power supply line 303, and the external energy-transmission device 304. The patient's skin 305, generally shown by a vertical line, separates the interior of the patient 102 to the right of the line from the exterior to the left of the line.

Figure 6:
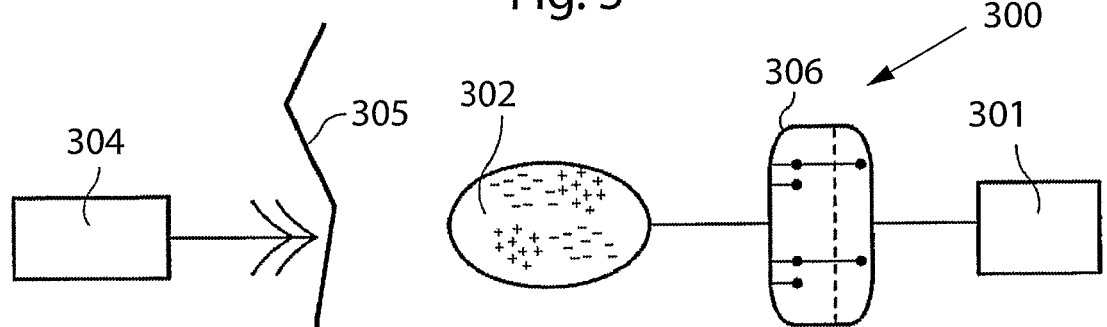

FIG. 6 shows an embodiment of the invention identical to that of FIG. 5, except that a reversing device in the form of an electric switch 306 operable for example by polarized energy also is implanted in the patient 102 for reversing the lifting device 301. When the switch 306 is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302, the electric switch 306 reverses the function performed by the lifting device 301.

Figure 7:
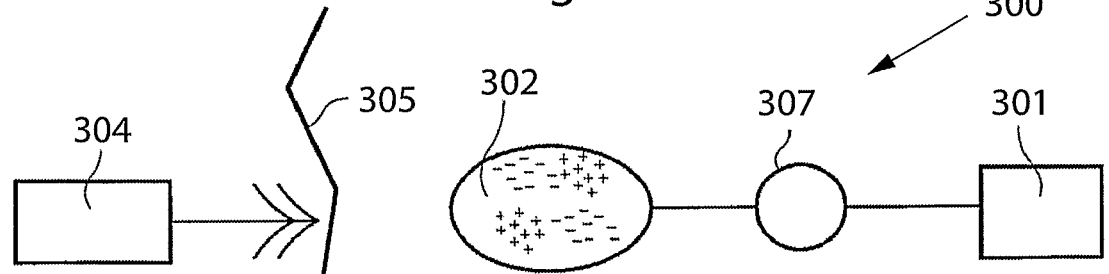

FIG. 7 shows an embodiment of the invention identical to that of FIG. 5, except that an operation device 307 implanted in the patient for operating the adjustable lifting device 301 is provided between the implanted energy-transforming device 302 and the lifting device 301. This operation device 307 can be in the form of a motor, such as an electric servomotor. The motor 307 is powered with energy from the implanted energy-transforming device 302, as the remote control of the external energy-transmission device 304 transmits a wireless signal to the receiver of the implanted energy-transforming device 302.

Figure 8:
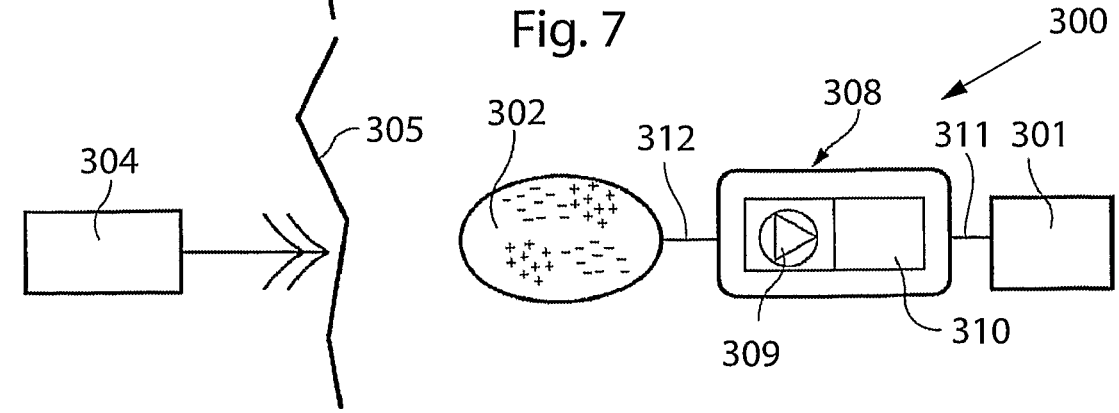

FIG. 8 shows an embodiment of the invention identical to that of FIG. 5, except that it also comprises an operation device in the form of an assembly 308, including a motor/pump unit 309 and a fluid reservoir 310 implanted in the patient 102. In this case, the lifting device 301 is hydraulically operated, i.e., hydraulic fluid is pumped by the motor/pump unit 309 from the fluid reservoir 310 through a conduit 311 to the lifting device 301 to operate the lifting device 301, and hydraulic fluid is pumped by the motor/pump unit 309 back from the lifting device 301 to the fluid reservoir 310 to return the lifting device 301 to a starting position. The implanted energy-transforming device 302 transforms wireless energy into a current, for example a polarized current, for powering the motor/pump unit 309 via an electric power supply line 312.

Instead of a hydraulically operated lifting device 301, it is also envisaged that the operation device comprises a pneumatic operation device. In this case, the pneumatic fluid can be pressurized air to be used for regulation and the fluid reservoir is replaced by an air chamber.

In all of these embodiments the energy-transforming device 302 may include a rechargeable accumulator, like a battery or a capacitor, to be charged by the wireless energy and supply energy for any energy consuming part of the lifting device 301.

As an alternative, the wireless remote control 304 described above may be replaced by manual control of any implanted part to make contact with by the patient's hand, most likely indirect, for example, a press button 338 (FIG. 1) placed under the skin 305.

Figure 9:
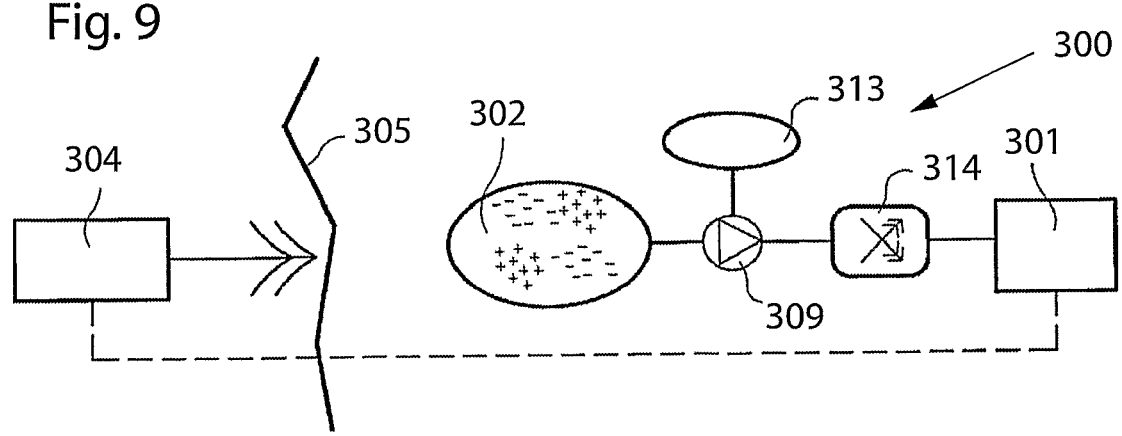

FIG. 9 shows an embodiment of the invention comprising the external energy-transmission device 304 with its wireless remote control, the lifting device 301, in this case hydraulically operated, and the implanted energy-transforming device 302, and further comprising a hydraulic fluid reservoir 313, a motor/pump unit 309 and an reversing device in the form of a hydraulic valve shifting device 314, all implanted in the patient. Of course, the hydraulic operation could easily be performed by just changing the pumping direction, and the hydraulic valve may, therefore, be omitted. The remote control may be a device separated from the external energy-transmission device or included in the same. The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and the lifting device 301. The remote control of the external energy-transmission device 304 controls the hydraulic valve shifting device 314 to shift the hydraulic fluid flow direction between one direction, in which the fluid is pumped by the motor/pump unit 309 from the hydraulic fluid reservoir 313 to the lifting device 301 to operate the device 301, and another opposite direction in which the fluid is pumped by the motor/pump unit 309 back from the lifting device 301 to the hydraulic fluid reservoir 313 to return the device 301 to a starting position.

Figure 10:
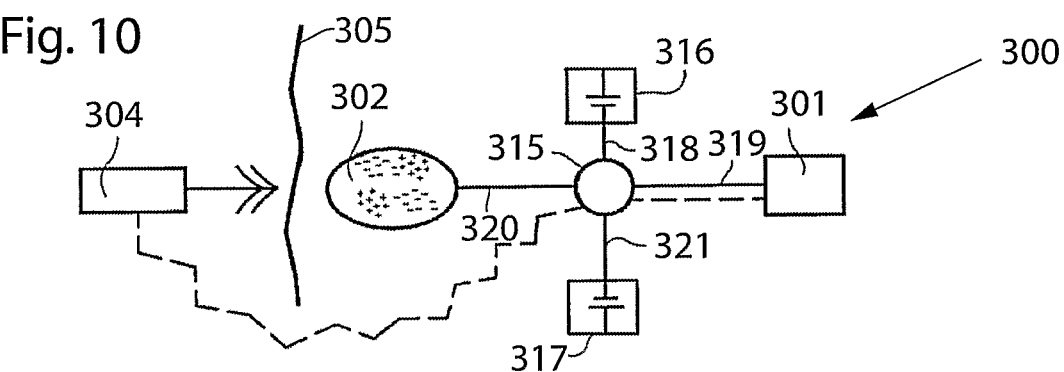

FIG. 10 shows an embodiment of the invention comprising the external energy-transmission device 304 with its wireless remote control, the adjustable lifting device 301, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the lifting device 301. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the lifting device 301.

The internal control unit is preferably programmable from outside the patient's body. In one embodiment, the internal control unit is programmed to regulate the lifting device 301 according to a pre-programmed time-schedule or to input from any sensor sensing any possible physical parameter of the patient 102 or any functional parameter of the lifting device 301.

In accordance with an alternative embodiment, the capacitor 317 in the embodiment of FIG. 10 may be omitted. In accordance with another alternative embodiment, the accumulator 316 in this embodiment may be omitted.

Figure 11:
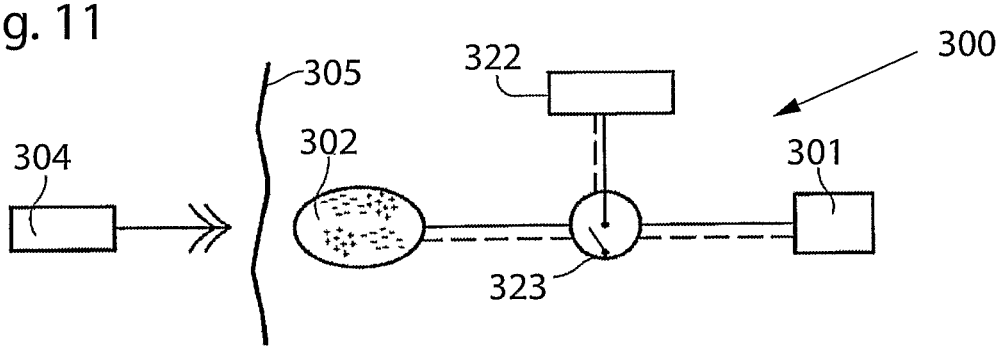

FIG. 11 shows an embodiment of the invention that is identical to that of FIG. 5, except for a battery 322 for supplying energy for the operation of the lifting device 301 and an electric switch 323 for switching the operation of the lifting device 301 also are implanted in the patient 102. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the lifting device 301.

Figure 12:
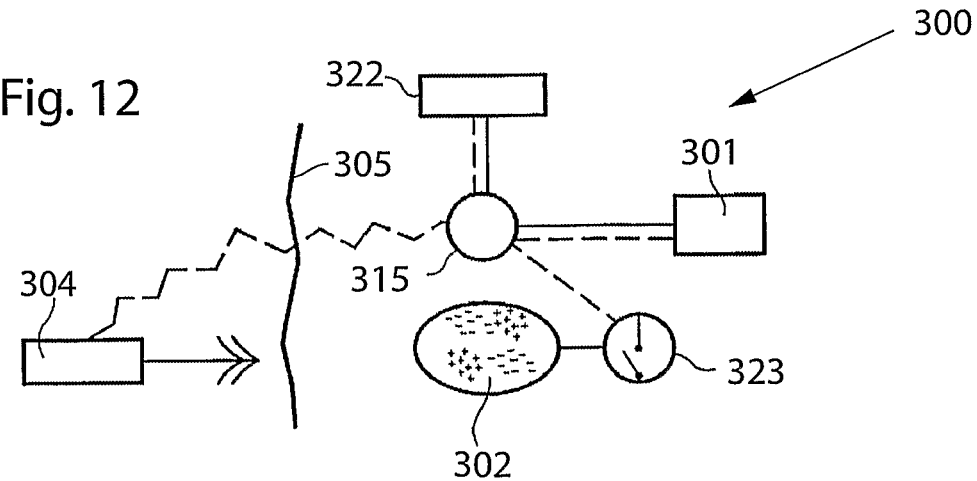

FIG. 12 shows an embodiment of the invention identical to that of FIG. 11, except that an internal control unit 315 controllable by the wireless remote control of the external energy-transmission device 304 also is implanted in the patient 102. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the adjustable lifting device 301.

Figure 13:
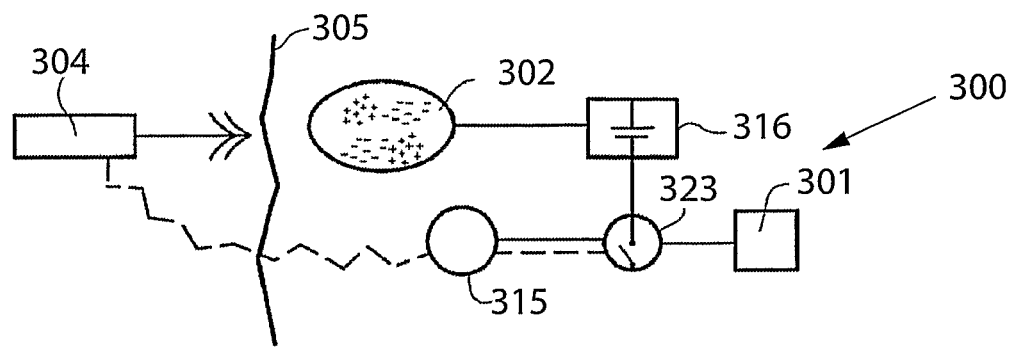

FIG. 13 shows an embodiment of the invention identical to that of FIG. 12, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the lifting device 301. The accumulator may be combined with or replaced by a capacitor.

Figure 14:
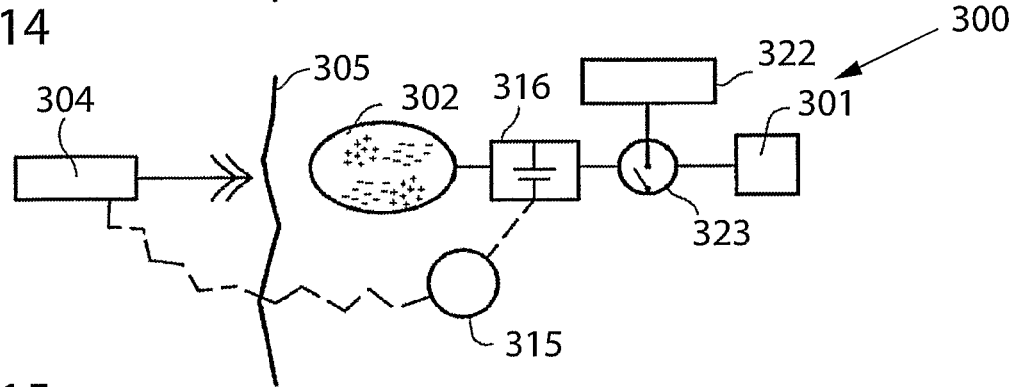

FIG. 14 shows an embodiment of the invention identical to that of FIG. 13, except that a battery 322 also is implanted in the patient 102 and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the adjustable lifting device 301.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the lifting device 301.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 15:
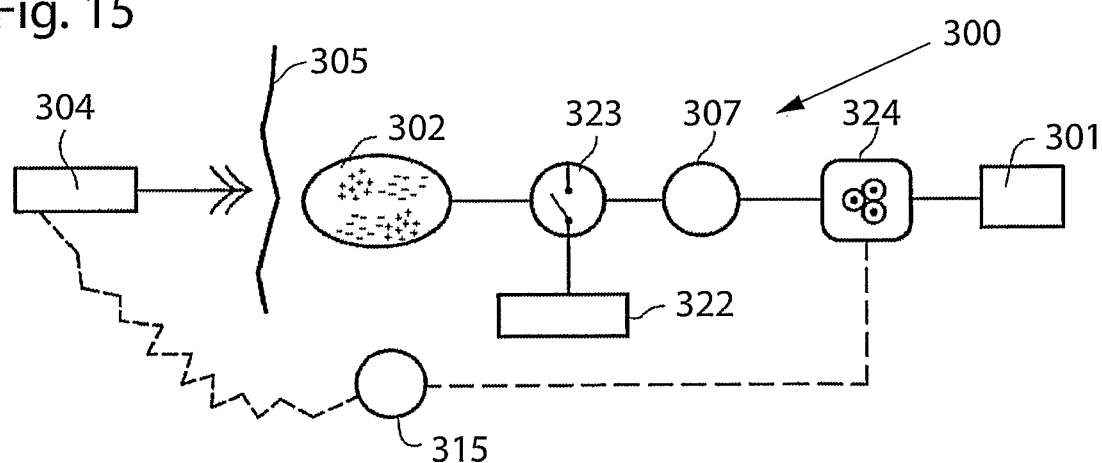

FIG. 15 shows an embodiment of the invention identical to that of FIG. 11, except for a motor 307, a mechanical reversing device in the form of a gear box 324, and an internal control unit 315 for controlling the gear box 324 that are also implanted in the patient. The internal control unit 315 controls the gear box 324 to reverse the function performed by the lifting device 301 (mechanically operated). Even simpler is to switch the direction of the motor electronically. The gear box interpreted in its broadest embodiment may stand for a servo arrangement saving force for the operation device in favor of longer stroke to act.

Figure 16:
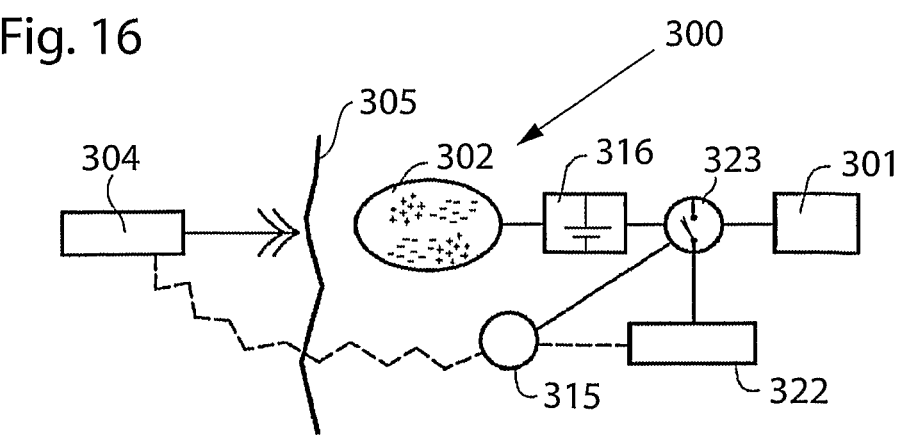

FIG. 16 shows an embodiment of the invention identical to that of FIG. 15, except that the implanted components are interconnected differently. Thus, in this embodiment, the internal control unit 315 is powered by the battery 322 when the accumulator 316, suitably a capacitor, activates the electric switch 323 to switch to an on mode. When the electric switch 323 is in its on mode, the internal control unit 315 is permitted to control the battery 322 to supply, or not supply, energy for the operation of the lifting device 301.

Figure 17:
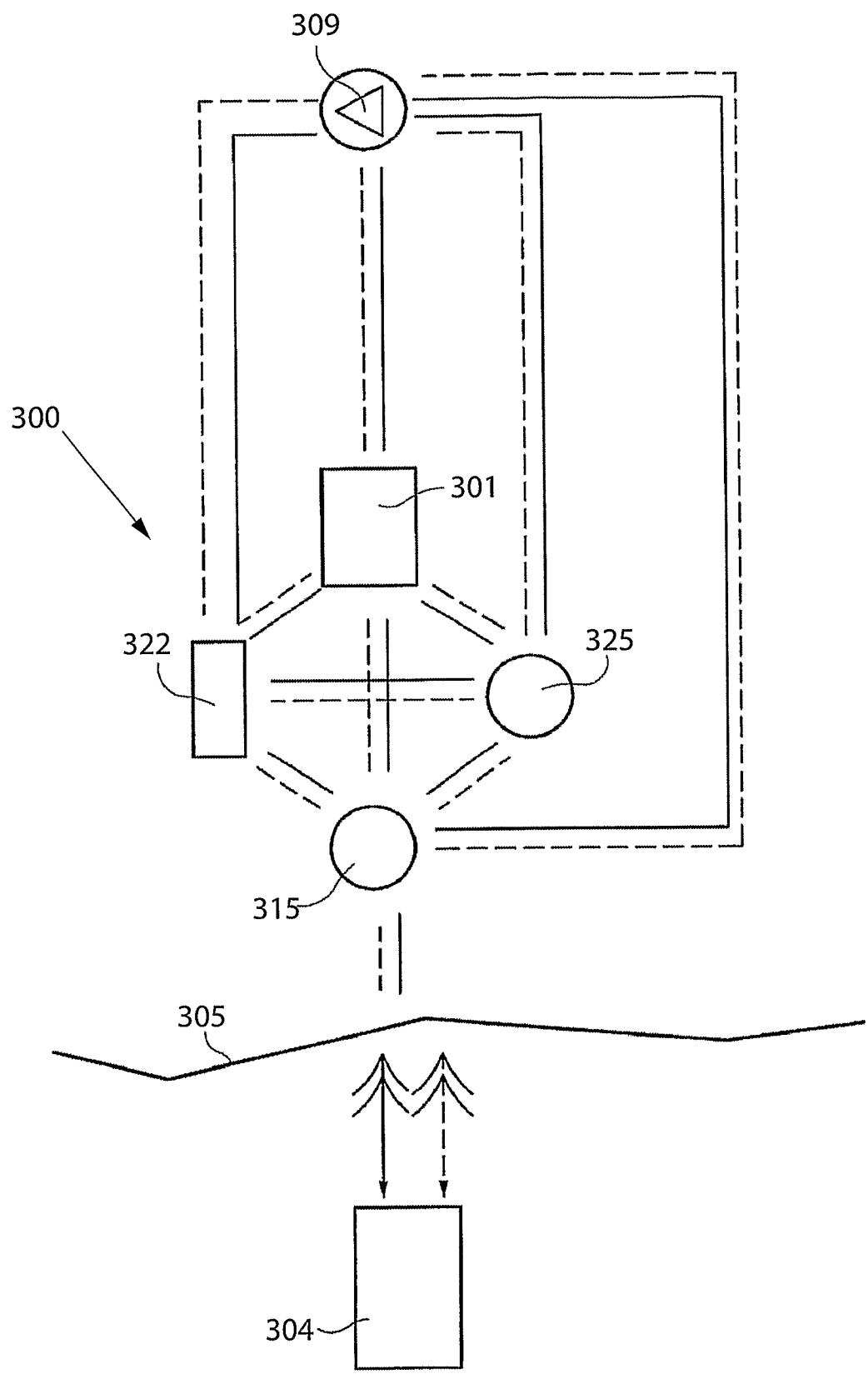

FIG. 17 schematically shows conceivable combinations of implanted components of the apparatus for achieving various communication options. Basically, there are the lifting device 301, the internal control unit 315, motor or pump unit 309, and the external energy-transmission device 304, including the external wireless remote control. As already described above, the wireless remote control transmits a control signal which is received by the internal control unit 315, which, in turn, controls the various implanted components of the apparatus.

A feedback device, preferably comprising a sensor or measuring device 325, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of electricity, any electrical parameter, pressure, volume, diameter, stretch, elongation, extension, movement, bending, elasticity, temperature and flow.

The feedback may be sent to the internal control unit or out to an external control unit, preferably via the internal control unit. Feedback may be sent out from the body via the energy transfer apparatus or a separate communication apparatus with receiver and transmitters.

The internal control unit 315, or alternatively the external wireless remote control of the external energy-transmission device 304, may control the lifting device 301, in response to signals from the sensor 325. A transceiver may be combined with the sensor 325 for sending information on the sensed physical parameter to the external wireless remote control. The wireless remote control may comprise a signal transmitter or transceiver 340 (FIG. 1) and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the lifting device 301 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to the charging process is sent and the energy supply is changed accordingly.

Figure 18:
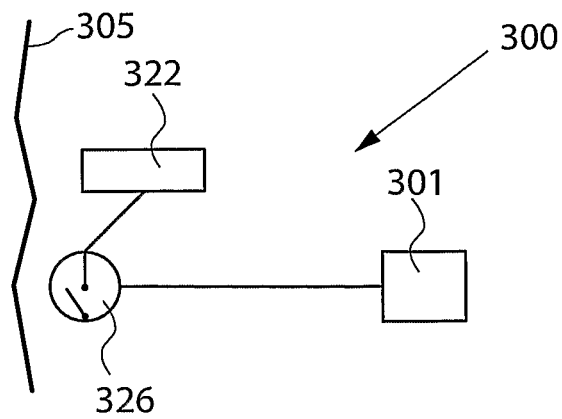

FIG. 18 shows an alternative embodiment wherein the adjustable lifting device 301 is controlled from outside the patient's body. The apparatus 300 comprises a battery 322 connected to the lifting device 301 via a subcutaneous electric switch 326. Thus, the control of the lifting device 301 is performed non-invasively by manually pressing the subcutaneous switch, whereby the operation of the lifting device 301 is switched on and off. It will be appreciated that the shown embodiment is a simplification and that additional components, such as an internal control unit or any other part disclosed in the present application can be added to the apparatus 300. Two subcutaneous switches may also be used. In the preferred embodiment, one implanted switch sends information to the internal control unit to perform a certain predetermined performance, and when the patient press the switch again the performance is reversed.

Figure 19:
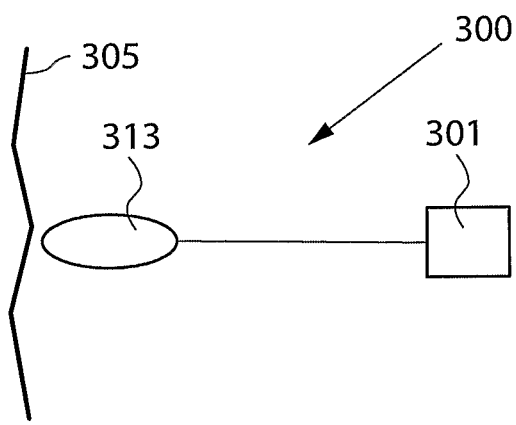

FIG. 19 shows an alternative embodiment, wherein the apparatus 300 comprises a hydraulic fluid reservoir 313 hydraulically connected to the lifting device 301. Non-invasive regulation is performed by manually pressing the hydraulic reservoir connected to the lifting device 301.

The apparatus 300 may include an external data communicator and an implantable internal data communicator communicating with the external data communicator. The internal communicator feeds data related to the apparatus or the patient to the external data communicator and/or the external data communicator feeds data to the internal data communicator.

Figure 20:
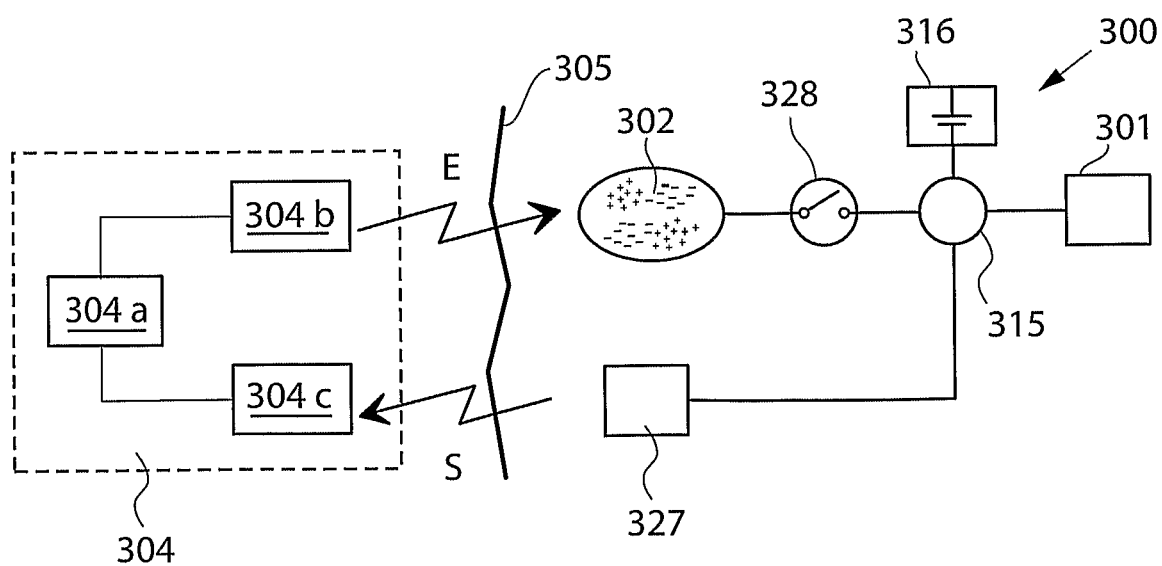
FIG. 20 is a schematic block diagram illustrating an arrangement for supplying an accurate amount of energy used for the operation of the apparatus shown in FIGS. 1-4.

FIG. 20 schematically illustrates an arrangement of the apparatus 300 that is capable of sending information from inside the patient's body to the outside thereof to give feedback information related to at least one functional parameter of the apparatus 300 or the lifting device 301, or related to a physical parameter of the patient, in order to supply an accurate amount of energy to an implanted internal energy receiver 302 connected to implanted energy consuming components of the lifting device 301. Such an energy receiver 302 may include an energy source and/or an energy-transforming device. Briefly described, wireless energy is transmitted from an external energy source 304a located outside the patient and is received by the internal energy receiver 302 located inside the patient. The internal energy receiver is adapted to directly or indirectly supply received energy to the energy consuming components of the lifting device 301 via a switch 326. An energy balance is determined between the energy received by the internal energy receiver 302 and the energy used for the lifting device 301, and the transmission of wireless energy is then controlled based on the determined energy balance. The energy balance thus provides an accurate indication of the correct amount of energy needed, which is sufficient to operate the adjustable lifting device 301 properly, but without causing undue temperature rise.

In FIG. 20, the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g., preferably in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil, which can be used to power the implanted energy consuming components of the apparatus, e.g., after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the lifting device 301. The internal control unit 315 may thus be arranged to receive various measurements obtained by suitable sensors or the like, not shown, measuring certain characteristics of the lifting device 301, somehow reflecting the required amount of energy needed for proper operation of the lifting device 301. Moreover, the current condition of the patient 102 may also be detected by means of suitable measuring devices or sensors, in order to provide parameters reflecting the patient's condition. Hence, such characteristics and/or parameters may be related to the current state of the lifting device 301, such as power consumption, operational mode and temperature, as well as the patient's condition reflected by parameters such as body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the lifting device 301. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the lifting device 301, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the lifting device 301, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b, wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution according to the arrangement of FIG. 20 employs the feed back of information indicating the required energy, which is more efficient than previous solutions because it is based on the actual use of energy that is compared to the received energy, e.g., with respect to the amount of energy, the energy difference, or the energy receiving rate as compared to the energy rate used by implanted energy consuming components of the apparatus 300. The apparatus 300 may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus 300.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external energy source 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system, including receivers and transmitters, or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 20, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 20 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b, instead depending on the implementation, as mentioned above. In that case, the control signal may carry measurement results from various sensors. The amount of energy emitted from the external energy source 304a can then be regulated by the external control unit 304b, based on the determined energy balance, e.g., in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing, in this case, the amount of energy transferred with the amount of energy received. For example, if the external coil is moved, the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 21:
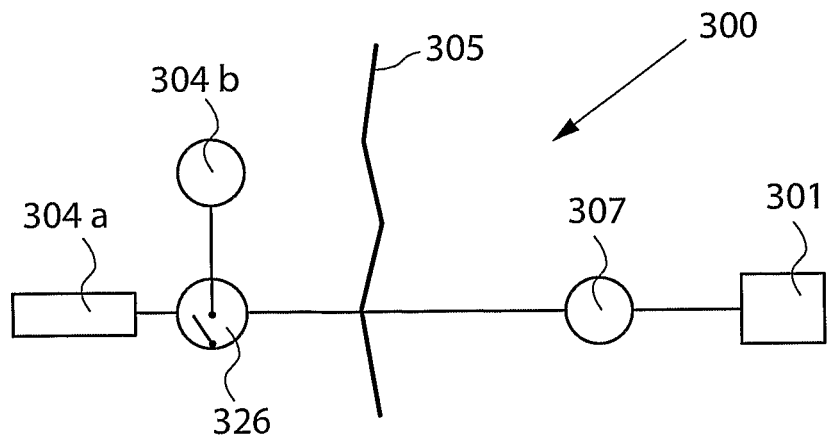
FIG. 21 schematically shows an embodiment of the apparatus, in which the apparatus is operated with wire bound energy.

With reference to FIG. 21, although wireless transfer of energy for operating the apparatus has been described above to enable non-invasive operation, it will be appreciated that the apparatus can be operated with wire bound energy as well. Such an example is shown in FIG. 21, wherein an external switch 326 is interconnected between the external energy source 304a and an operation device, such as an electric motor 307 operating the lifting device 301. An external control unit 304b controls the operation of the external switch 326 to effect proper operation of the lifting device 301.

Figure 22:
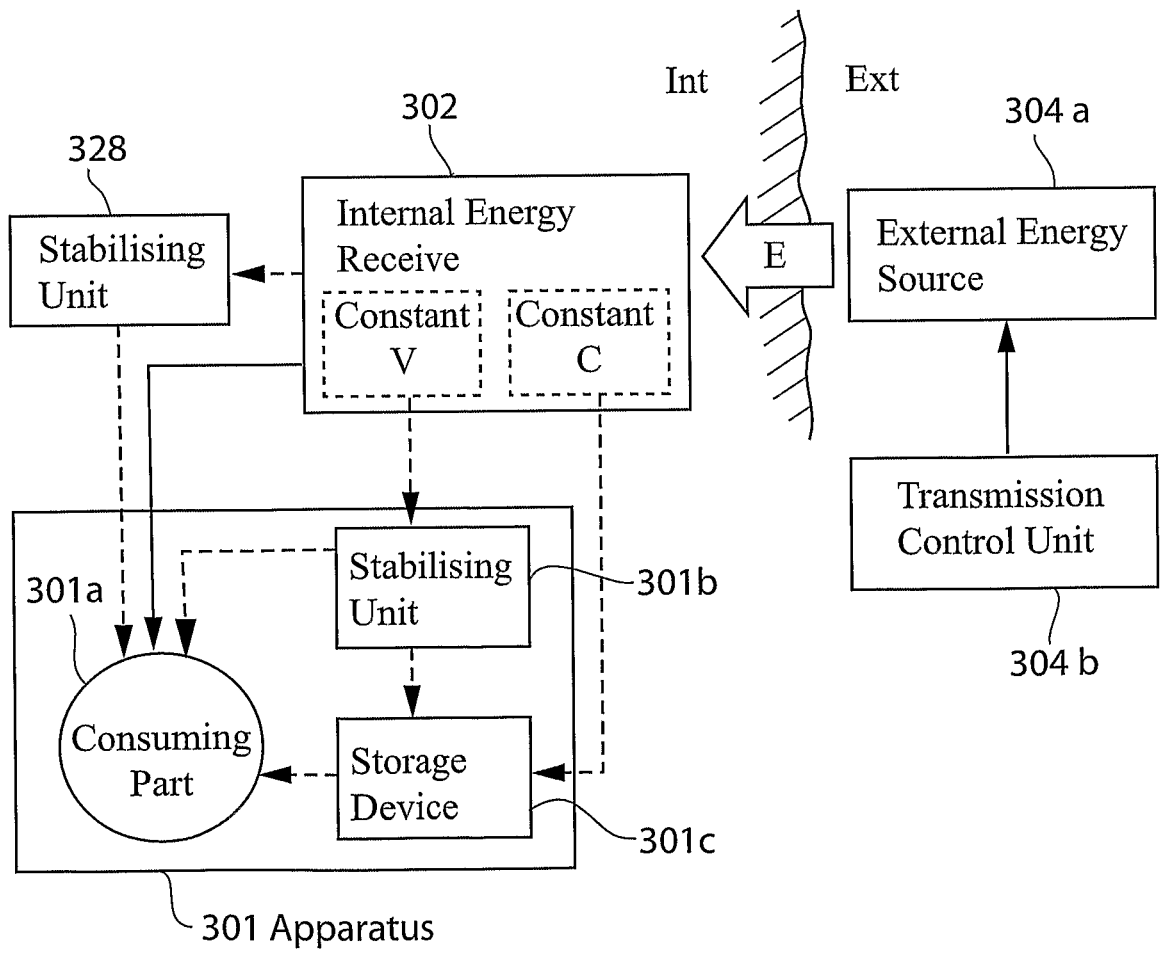
FIG. 22 is a more detailed block diagram of an arrangement for controlling the transmission of wireless energy used for the operation of the apparatus shown in FIGS. 1-3.

FIG. 22 illustrates different embodiments for how received energy can be supplied to and used by the lifting device 301. Similar to the example of FIG. 20, an internal energy receiver 302 receives wireless energy E from an external energy source 304a, which is controlled by a transmission control unit 304b. The internal energy receiver 302 may comprise a constant voltage circuit, indicated as a dashed box "constant V" in the figure, for supplying energy at constant voltage to the lifting device 301. The internal energy receiver 302 may further comprise a constant current circuit, indicated as a dashed box "constant C" in the figure, for supplying energy at constant current to the lifting device 301.

The adjustable lifting device 301 comprises an energy consuming part 301a, which may be a motor, pump, restriction device, or any other medical appliance that requires energy for its electrical operation. The lifting device 301 may further comprise an energy storage device 301b for storing energy supplied from the internal energy receiver 302. Thus, the supplied energy may be directly consumed by the energy consuming part 301a, or stored by the energy storage device 301b, or the supplied energy may be partly consumed and partly stored. The lifting device 301 may further comprise an energy stabilizing unit 301c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the lifting device 301, before being consumed and/or stored by the lifting device 301. Alternatively, the energy stabilizing unit 328 may be integrated in the internal energy receiver 302. In either case, the energy stabilizing unit 328 may comprise a constant voltage circuit and/or a constant current circuit.

It should be noted that FIGS. 20 and 22 illustrate some possible, but non-limiting, implementation options regarding how the various shown functional components and elements can be arranged and connected to each other. However, the skilled person will readily appreciate that many variations and modifications can be made within the scope of the present invention.

Figure 23:
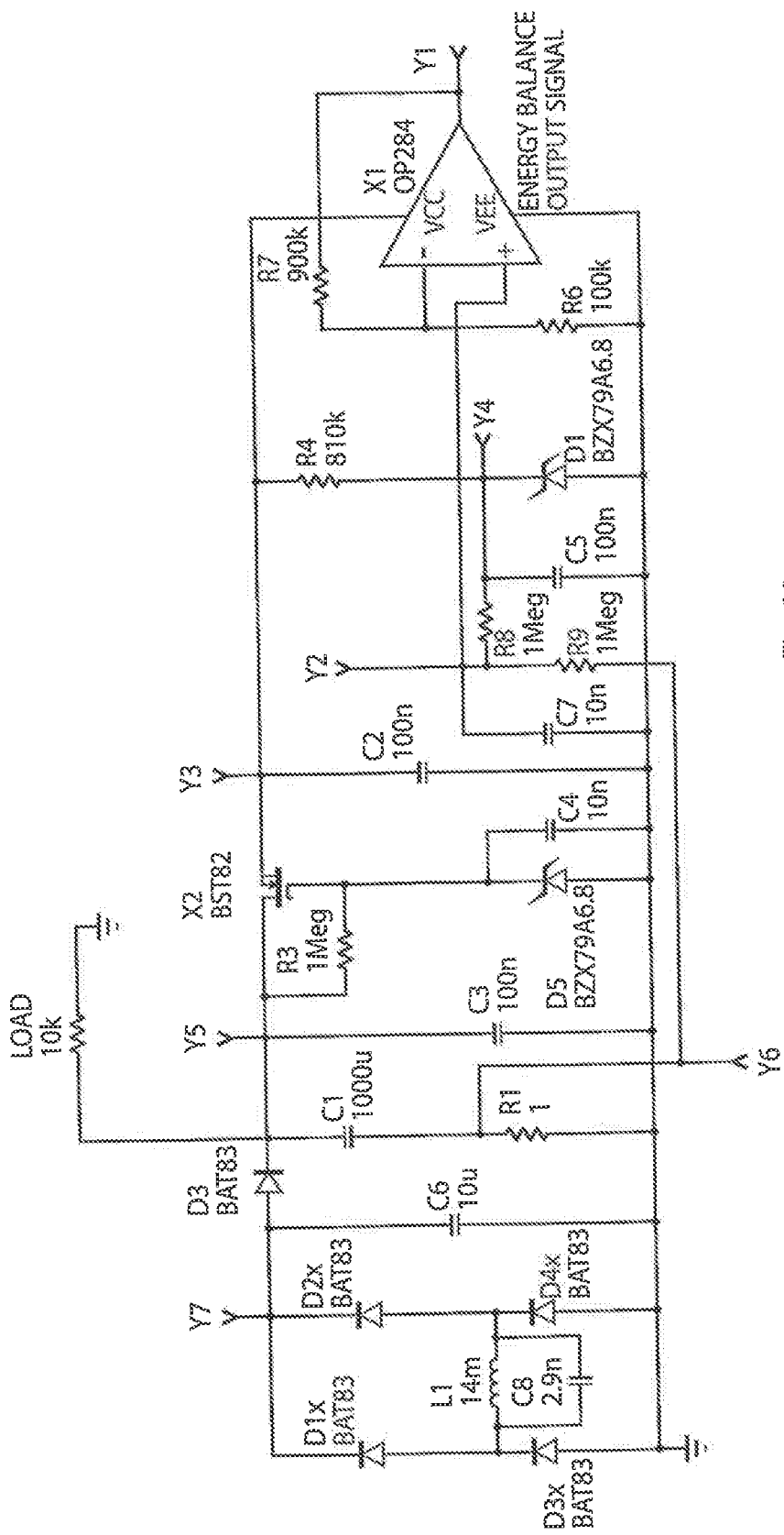
FIG. 23 is a circuit for the arrangement shown in FIG. 19, according to a possible implementation example.

FIG. 23 schematically shows an energy balance measuring circuit of one of the proposed designs of the apparatus for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 23 shows a circuit implementation for a system that transfers energy to the implanted energy components of the apparatus 300 of the present invention from outside of the patient's body using inductive energy transfer. An inductive energy transfer system typically uses an external transmitting coil and an internal receiving coil. The receiving coil, L1, is included in the schematic FIG. 23. The transmitting parts of the system are excluded.

The implementation of the general concept of energy balance and the way the information is transmitted to the external energy transmitter can of course be implemented in numerous different ways. The schematic FIG. 23 and the above described method of evaluating and transmitting the information should only be regarded as examples of how to implement the control system.

Circuit Details

In FIG. 23 the symbols Y1, Y2, Y3 and so on symbolize test points within the circuit. The components in the diagram and their respective values are values that work in this particular implementation which of course is only one of an infinite number of possible design solutions. Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 6 could be incorporated in any of the embodiments of FIGS. 12-18, the hydraulic valve shifting device 314 of FIG. 12 could be incorporated in the embodiment of FIG. 11, and the gear box 324 could be incorporated in the embodiment of FIG. 10. It should be noted that the switch simply could mean any electronic circuit or component.

The embodiments described in connection with FIGS. 20, 22 and 23 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the lifting device 301 may be consumed to operate the lifting device 301, and/or stored in at least one energy storage device of the lifting device 301.

When electrical and/or physical parameters of the lifting device 301 and/or physical parameters of the patient are determined, the energy may be transmitted for consumption and storage according to a transmission rate per time unit which is determined based on the parameters. The total amount of transmitted energy may also be determined based on the parameters.

When a difference is detected between the total amount of energy received by the internal energy receiver and the total amount of consumed and/or stored energy, and the detected difference is related to the integral over time of at least one measured electrical parameter related to the energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus 300. In its broadest sense, the apparatus 300 comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The apparatus further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the apparatus may comprise any of the following.

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of the detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on the parameters. The determination device also determines the total amount of transmitted energy based on the parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, the train having a first electrical pulse at the start of the pulse train and having a second electrical pulse at the end of the pulse train.

The lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 24-30c show various ways of arranging hydraulic or pneumatic powering of the urinary treatment apparatus implanted in a patient. Specifically, FIGS. 24-27 show in more detail block diagrams of four different ways of hydraulically or pneumatically powering an implanted apparatus according to the invention.

Figure 24:
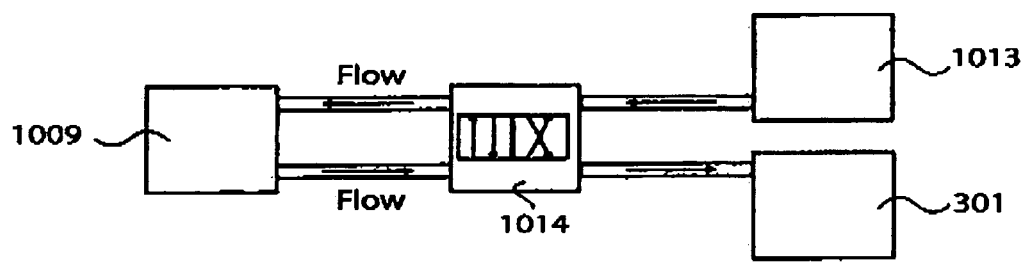
FIGS. 24-30c show various ways of arranging hydraulic or pneumatic powering of the urinary treatment apparatus implanted in a patient.

FIG. 24 shows an apparatus as described above with the apparatus comprising the implanted variable lifting device 301, and further comprising a separate regulation reservoir 1013, a one way pump 1009 and an alternate valve 1014.

Figure 25:

FIG. 25 shows the variable lifting device 301 and a fluid reservoir 1013. By moving the wall of the regulation reservoir or changing the size of the same in any other different way, the adjustment of the device 301 may be performed without any valve, just free passage of fluid any time by moving the reservoir wall.

Figure 26:
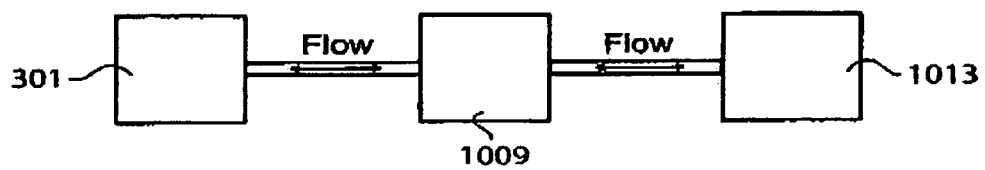

FIG. 26 shows the device 301, a two way pump 1009 and the regulation reservoir 1013.

Figure 27:
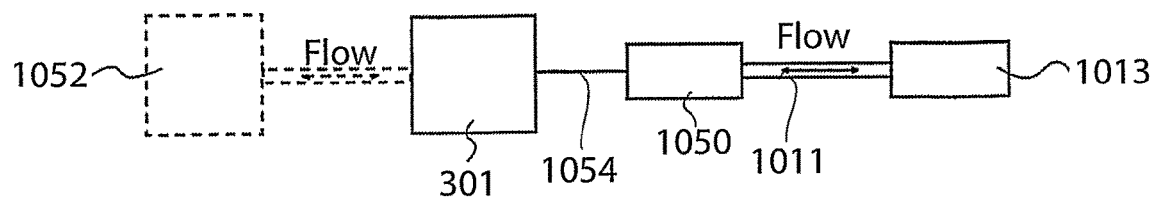

FIG. 27 shows a block diagram of a reversed servo system with a first closed system controlling a second closed system. The servo system comprises a regulation reservoir 1013 and a servo reservoir 1050. The servo reservoir 1050 mechanically controls the implanted lifting device 301 via a mechanical interconnection 1054. The device in this embodiment has an expandable and contractible cavity. This cavity is preferably expanded or contracted by supplying hydraulic fluid from the larger adjustable reservoir 1052 in fluid connection with the lifting device 301. Alternatively, the cavity contains compressible gas, which can be compressed and expanded under the control of the servo reservoir 1050.

The servo reservoir 1050 can also be part of the lifting device 301.

Figure 28A:
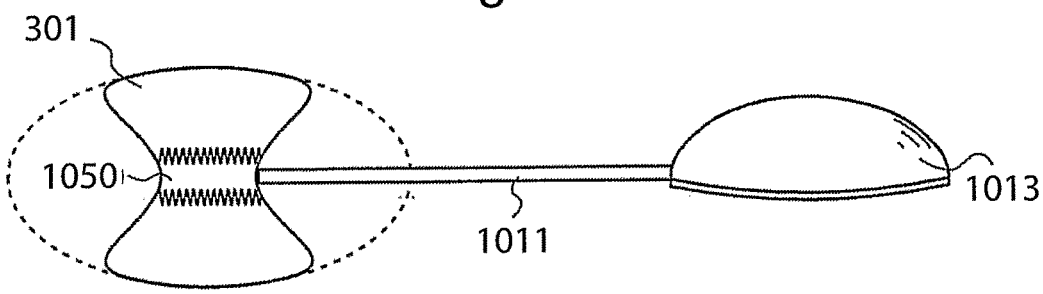
Figure 28B:
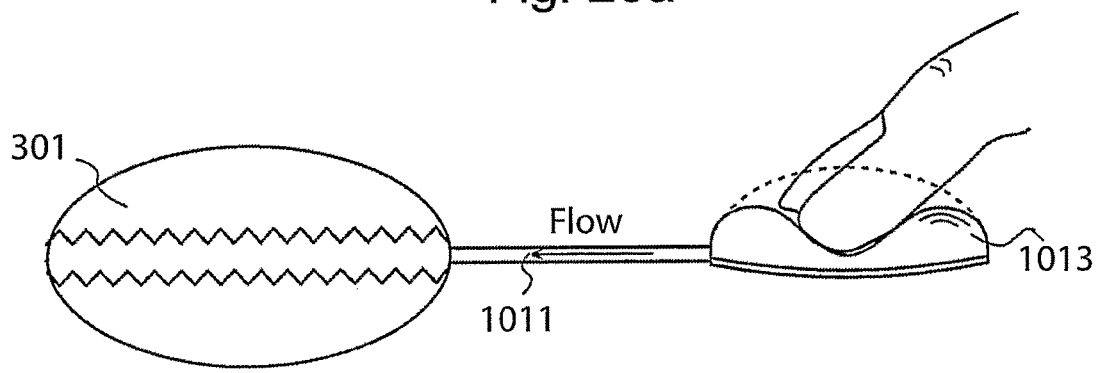
Figure 28C:
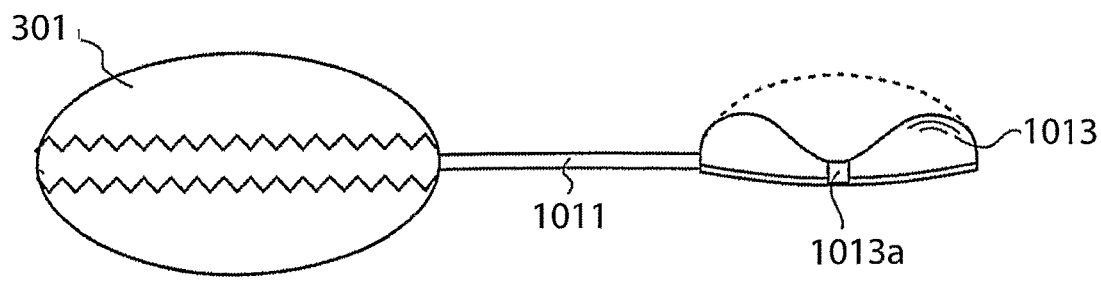

In one embodiment, the regulation reservoir is placed subcutaneous under the patient's skin and is operated by pushing the outer surface thereof by means of a finger. This system is illustrated in FIGS. 28a-c. In FIG. 28a, a flexible subcutaneous regulation reservoir 1013 is shown connected to a bulge shaped servo reservoir 1050 by means of a conduit 1011. This bellow shaped servo reservoir 1050 is comprised in a flexible device 301. In the state shown in FIG. 28a, the servo reservoir 1050 contains a minimum of fluid and most fluid is found in the regulation reservoir 1013. Due to the mechanical interconnection between the servo reservoir 1050 and the device 301, the outer shape of the device 301 is contracted, i.e., it occupies less than its maximum volume. This maximum volume is shown with dashed lines in the figure.

FIG. 28b shows a state wherein a user, such as the patient in with the device 301 is implanted, presses the regulation reservoir 1013 so that fluid contained therein is brought to flow through the conduit 1011 and into the servo reservoir 1050, which, thanks to its bellow shape, expands longitudinally. This expansion, in turn, expands the device 301 so that it occupies its maximum volume, thereby stretching interconnecting part 334 (shown in FIGS. 1-3), which it contacts.

The regulation reservoir 1013 is preferably provided with means 1013a for keeping its shape after compression. This means, which is schematically shown in the figure, will thus keep the interconnecting part 334 in a stretched position also when the user releases the regulation reservoir. In this way, the regulation reservoir essentially operates as an on/off switch for the apparatus.

Figure 29:
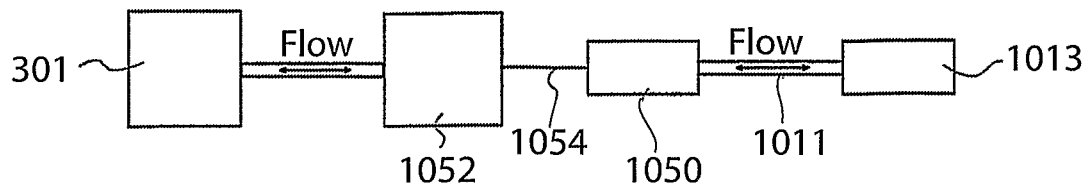

An alternative embodiment of hydraulic or pneumatic operation will now be described with reference to FIGS. 29 and 30a-c. The block diagram shown in FIG. 29 is comprised with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. The implanted adjustable lifting device 301, having an expandable/contactable interconnecting part 334, is in turn controlled by the larger adjustable reservoir 1052 by supply of hydraulic fluid from the larger adjustable reservoir 1052 in fluid connection with the adjustable lifting device 301.

Figure 30A:
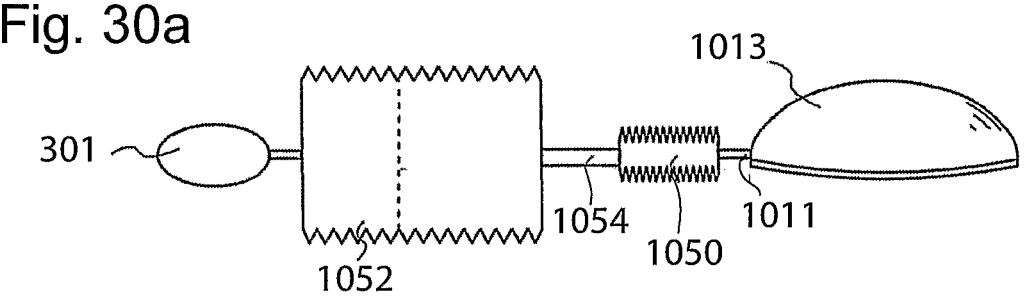
Figure 30B:
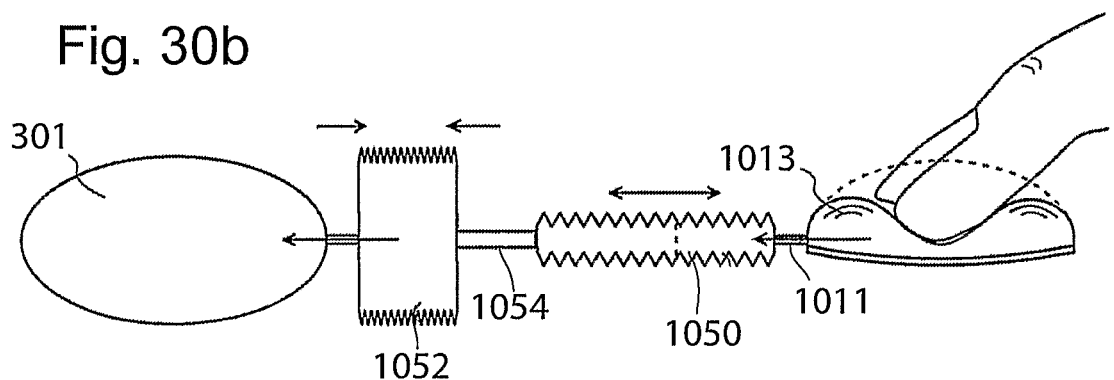
Figure 30C:
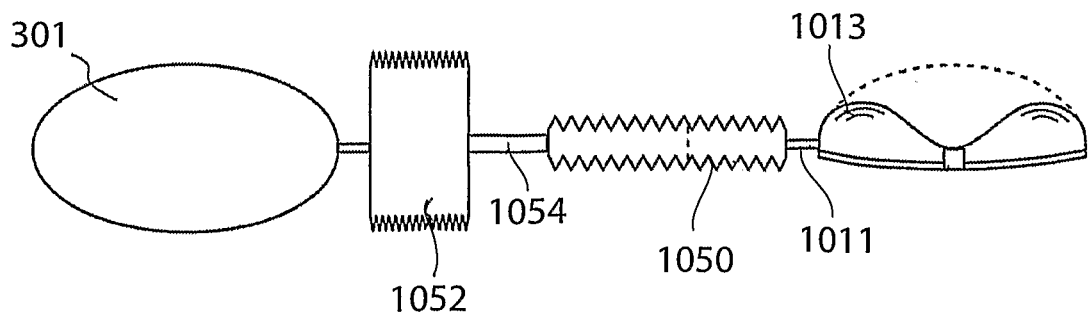

An example of this embodiment will now be described with reference to FIG. 30a-c. Like in the previous embodiment, the regulation reservoir is placed subcutaneously under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 30a, the servo reservoir 1050 contains a minimum of fluid and most fluid is found in the regulation reservoir 1013.

The servo reservoir 1050 is mechanically connected to a larger adjustable reservoir 1052, in this example, also having a bellow shape, but with a larger diameter than the servo reservoir 1050. The larger adjustable reservoir 1052 is in fluid connection with the adjustable lifting device 301. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the lifting device 301. In other words, in this reversed servo, a small volume in the regulation reservoir is compressed with a higher force and this creates a movement of a larger total area with less force per area unit.

Like in the previous embodiment described above with reference to FIG. 28a-c, the regulation reservoir 1013 is preferably provided with means 1013a for keeping its shape after compression. This shape keeping means, which is schematically shown in the figure, will thus keep the interconnecting part 334 in a stretched position also when the user releases the regulation reservoir. In this way, the regulation reservoir essentially operates as an on/off switch for the apparatus 300.

Although the different parts described above have specific placements on the drawings it should be understood that these placements might vary, depending on the application.

It should be noted that any embodiment in any combination that is disclosed in this application may be used, especially but not limited to, all the figures and detailed descriptions thereto.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. An apparatus to treat urinary incontinence in a patient, comprising:
at least one adjustable U-shaped lifting device adapted to lift a urethra or neck of a urine bladder, thereby affecting the patient's incontinence,
an internal energy receiver adapted to receive wireless energy from a source of wireless magnetic or electromagnetic energy located externally to the patient,
a motor being adapted to alternately increase and decrease the length of the U-shaped lifting device, wherein the internal energy receiver is connected to the motor and adapted to directly supply the received energy to the motor,
a temperature sensor for sensing at least one parameter being a body temperature of the patient or a temperature of the lifting device, and a control unit configured to receive information related to the at least one parameter during operation of the motor, and to control an amount of energy transferred between the source of wireless energy and the internal energy receiver during operation of the motor, based on said information, such that the amount of energy transferred can be directly controlled during operation of the motor on the basis of the temperature sensor information.

2. The apparatus according to claim 1, wherein the at least one adjustable U-shaped lifting device is adapted to be placed at least partly according to at least one of:
    below a pubis bone and lift the urethra from a point below the pubis bone when the patient is standing,
    partly into the pubis bone and lift the urethra from a point attached to the pubis bone of the patient, and
    above the pubis bone of the patient when standing, to lift the urethra from a point above the pubis bone when the patient is standing.

3. The apparatus according to claim 1, wherein the at least one adjustable U-shaped lifting device is adapted to be placed in a female or male patient.

4. The apparatus according to claim 1, wherein the at least one adjustable U-shaped lifting device comprises a first and a second fixation device and an interconnecting part extending between the first and second fixation devices, wherein the at least one adjustable U-shaped lifting device is adapted to adjust at least one of:
    a distance between a first fixation position of the first fixation device and the urethra, wherein the first fixation device is adapted to be fixed to a pubis bone of the patient, and
    a distance between a second fixation position of the second fixation device and the urethra, wherein a second fixation point is adapted to be fixed to a pubis bone of the patient, and
    wherein the first fixation or second fixation devices are adapted to be adjustable.

5. The apparatus according to claim 4, wherein the first fixation device, the second fixation device or the first and second fixation devices is/are adapted to keep the at least one adjustable U-shaped lifting device in place by sutures or staples between the device and human tissue or bone.

6. The apparatus according to claim 4, wherein the first fixation device, the second fixation device, or the first and second fixation devices is/are connected by the interconnecting part being in a loop and adapted to keep the at least one adjustable U-shaped lifting device in place by the loop including human tissue, wherein the at least one adjustable U-shaped lifting device is adapted to be adjusted by changing a size of the loop, and wherein a loop adjustment adjusts the lift of the urethra.

7. The apparatus according to claim 6, wherein the first and second fixation devices are adapted to lift the urethra by changing a length of the loop, when implanted.

8. The apparatus according to claim 4, wherein the at least one adjustable U-shaped lifting device is adapted to be kept in place by invagination of human tissue by tissue-to-tissue sutures or staples.

9. The apparatus according to claim 4, wherein the interconnecting part is adapted to have a u-shaped form, to include the urethra inside the u-shape form when implanted, and adapted to lift the urethra by reducing a length of the u-shaped interconnecting part.

10. The apparatus according to claim 4, wherein the first fixation device, second fixation device, or first and second fixation devices comprise a structure adapted to be in contact with a human tissue to promote growth of human tissue in the structure to secure the long term placement of the at least one adjustable U-shaped lifting device.

11. The apparatus according to claim 10, wherein the structure comprises a net like structure.

12. The apparatus according to claim 1, wherein the at least one adjustable U-shaped lifting device is non-circumferential.

13. The apparatus according to claim 1, wherein the at least one adjustable U-shaped lifting device forms a loop that is adapted to have any shape or form and lift the urethra placed inside the loop when implanted.

14. The apparatus according to claim 1, wherein the apparatus is further adapted to adjust a length of a lifting sling interconnecting part of the U-shaped lifting device to adjust the lift of the urethra or the urine bladder.

15. The apparatus according to claim 14, wherein the interconnecting part includes an adjustable part whose diameter, length or diameter and length can be adjusted to thereby adjust the level of lift of the urethra by changing the diameter, length or diameter and length of the adjustable part.

16. The apparatus according to claim 15, wherein the adjustable part, comprising a hydraulic adjustment, wherein the adjustable part comprises a fillable reservoir adapted to be filled with a fluid from a second reservoir so as to adjust at least one of the length and diameter of the adjustable part, wherein the apparatus comprising, a hydraulic regulated at least one adjustable lifting device comprising at least one chamber and, further comprising a hydraulic reservoir, wherein the device is adapted to be non-invasively regulated by moving liquid or air from the reservoir to the at least one chamber.

17. The apparatus according to claim 16, wherein the reservoir is regulated by moving a wall of the reservoir, comprising a motor adapted to move the wall of the reservoir.

18. The apparatus according to claim 14, wherein the at least one adjustable U-shaped lifting device is adapted to post-operatively and non-invasively adjust a level of lift of the urethra by changing at least one of a width and a length of the interconnecting part.

19. The apparatus according to claim 1, comprising a mechanically regulated device, adapted to use the motor for mechanically regulating the mechanically regulated device.

20. The apparatus according to claim 1, wherein the source of wireless magnetic or electromagnetic energy comprises an energy-transmission device which comprises a coil adapted to be placed externally to a human body, wherein the source of wireless magnetic or electromagnetic energy further comprises an electric circuit connected to power the external coil with electrical pulses to transmit the wireless energy, the electrical pulses having leading and trailing edges, the electric circuit adapted to vary at least one of: first time intervals between successive leading and trailing edges and second time intervals between successive trailing and leading edges of the electrical pulses to vary a power of the transmitted wireless energy, the motor receiving the transmitted wireless energy having a varied power.

21. The apparatus according to claim 1, comprising a wireless energy transmitter for transmitting wireless energy for use by any energy consuming part of the apparatus, directly or indirectly.

22. The apparatus according to claim 4, wherein the interconnecting part is extending uninterruptedly between the first and second fixation devices.

* * * * *